(12) United States Patent
Fisher

(10) Patent No.: US 6,677,152 B2
(45) Date of Patent: Jan. 13, 2004

(54) REVERSAL OF CANCER PHENOTYPE BY INHIBITING EXPRESSION OF PROSTATE TUMOR INDUCING GENE

(75) Inventor: Paul B. Fisher, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/263,178

(22) Filed: Mar. 5, 1999

(65) Prior Publication Data

US 2002/0090355 A1 Jul. 11, 2002

Related U.S. Application Data

(63) Continuation of application No. PCT/US97/15306, filed on Sep. 5, 1997, which is a continuation-in-part of application No. 08/708,206, filed on Sep. 6, 1996, now abandoned.

(51) Int. Cl.⁷ .............................................. C12N 15/63
(52) U.S. Cl. ..................... 435/320.1; 536/24.5; 435/325
(58) Field of Search ..................... 514/44; 435/320.1, 435/29, 325; 424/93.6; 436/24.5; 536/24.5

(56) References Cited

U.S. PATENT DOCUMENTS

| | | |
|---|---|---|
| 5,585,479 A | 12/1996 | Hoke et al. |
| 5,851,764 A | 12/1998 | Fisher et al. |

FOREIGN PATENT DOCUMENTS

| | | |
|---|---|---|
| WO | 9115580 | 10/1991 |
| WO | 9621671 | 7/1996 |

OTHER PUBLICATIONS

Plenat (J. Mol. Med. Today, vol. 2, No. 6:250–257, 1996).*
Stull et al., Pharmaceutical Res., vol. 12, pp. 465–483, 1995).*
Kausch et al. (The J. of Urology, vol. 168, pp. 239–247, 2002).*
Mastrangelo et al. (Seminars in Oncology, 1996, vol. 23, 1:4–21).*
Coghlan (New Scientist, vol. 148, 13–14, 1995).*
Eck et al., "Gene–based therapy." Goodman & Gilman's The Pharmacological Basis of Therapeutics– Ninth Edition McGraw–Hill: 77–101, 1996.*
Orkin et al., "Report and recommendations of the panel to assess the NIH investment in research on gene therapy." pp. 1–20, Dec. 1995.*
Crystal R. "Transfer of genes to humans: Early lessons and obstacles to success." Science, vol. 270: 404–410, 1995.*
Verma et al., "Gene therapy– promises, problems and prospects." Nature, vol. 389: 239–242, Sep. 1997.*
Deonarain M., "Ligand–targeted receptor–mediated vectors for gene delivery." Exp. Opin. Ther. Patents, vol. 8 (1): 53–69, 1998.*

Miller et al., "Targeted vectors for gene therapy."–FASEB, vol. 9:190–199, Feb. 1995.*
Ledley, Pharmaceutical Res., vol. 13: 1595–1614, 1996.*
Branch A D., TIBS 23: 45–50, Feb. 1998.*
Shen et al., Proc. Natl. Acad. Sci. USA, vol. 92 (15): 6778–6782, 1995.*
Merrick, W.C., (1992) "Mechanism and Regulation of Eukaryotic Protein Synthesis" *Microbiol Rev.*, 56:291–315 (Exhibit 1).
Hwang, Y.W., et al., (1989) "Mutagenesis of Bacterial Elongation Factor Tu at Lysine 136" *J.Biol.Chem.*, 264:8304–8306 (Exhibit 2).
Tapio, S., and Kurland, C.G., (1986) "Mutant EF–Tu increases missense error in vitro" *Mol. Gen. Genet.*, 205:186–188 (Exhibit 3).
Hughes, D. et al., (1987) "Mutants of elongation factor Tu promote ribosomal frameshifting and nonsense readthrough" *Embo. J.*, 6:4235–4239 (Exhibit 4).
Sandbaken, M.G., and Culberston, M.R., (1988) "Mutations in Elongation Factor EF–1α Affect the Frequency of meshifting and Amino Acid Misincorporation in Saccharomyces cerevisiae" *Genetics*, 120:923–934 (Exhibit 5); and.
Song, J.M. et al., (1989) "Elongation Factor EF–1α Gene Dosage Alters Translational Fidelity in Saccharomyces cerevisiae" *Mol. Cell. Biol.*, 9:4571–4575 (Exhibit 6).
De Benedetti et al. (1994). CHO Cells Transformed by the Translation Factor eIF–4E Display Increased c–myc Expression, but Require Overexpression of Max for Tumorigenicity. Molecular and Cellular Differentiation 2(4):347–371.
Loeb LA (1994). Microsatellite instability: marker of a mutator phenotype in cancer. Cancer Research 54:5059–5063.
Grant AG, Flomen RM, Tizard MLV, Grant DAW (1992). Differential screening of a human pancreatic adenocarcinoma λgt11 expression library has identified increased transcription of elongation factor EF–1α in tumour cells. Int. J. Cancer 51:740–745.

(List continued on next page.)

*Primary Examiner*—Dave T. Nguyen
(74) *Attorney, Agent, or Firm*—Baker Botts L.L.P.

(57) ABSTRACT

This invention provides a method for reversing cancer phenotype of a cancer cell by introducing an exogenous material which is capable of specifically recognizing either a Prostate Tumor Inducing Gene, RNA or gene product of the aforementioned gene into the cell under conditions permitting inhibition of the expression of the gene product so as to thereby reverse the cancerous phenotype of the cell. This invention also provides a method for reversing cancer phenotype of a cancer cell in a subject by introducing an exogenous material which is capable of specifically recognizing a Prostate Tumor Inducing Gene, RNA or gene product of the aforementioned gene into the subject's cancer cell under conditions permitting inhibition of the expression of the gene or function of the gene product in the subject's cell so as to thereby reverse the cancerous phenotype of the cell.

8 Claims, 11 Drawing Sheets

OTHER PUBLICATIONS

Lazaris–Karatzas A, Montine KS, Sonenberg N (1990). Malignant transformation by a eukaryotic initiation factor subunit that binds to mRNA 5' cap. *Nature* 345:544–547.
Sun et al. (1997) *Cancer Res.* 57, 18–23.
Jiang et al.(1996) *Proc. Natl. Acad. Sci. USA* 93, 9160–9165.
Jiang et al.(1995) *Oncogene* 10, 1855–1864.
Shen et al.(1995) *Proc. Natl. Acad. Sci. USA* 92, 6778–6782.
Su et al. (1995) *Int. J. Oncol.* 7, 1279–1284.
Israeli et al.(1994) *Cancer Res.* 54, 6306–6310.
Katz et al.(1994) *Urology* 43, 765–775.
Rabbits (1994) *Nature* 372, 143–149.
Jiang et al.(1993) *Mol. Cell. Different.* 1, 197–214.
Epstein et al.(1993) *Cancer* 71, 3582–3593.
Sonenberg (1993) *Curr. Biol.* 5, 955–960.
Stein and Cheng (1993) *Science* 261, 1004–1012.
Su et al.(1993) *Oncogene* 8, 1211–1219.
Lazaris–Karatzas and Sonenberg (1992) *Mol. Cell. Biol.* 12, 1234–1238.
Merrick (1992) *Microbiol. Rev.* 60, 291–315.
Neckers et al.(1992) *Crit. Rev. Oncog.* 3, 175–231.
Su et al.(1992) *Anticancer Res.* 12, 297–304.
Tatsuka et al.(1992) *Nature* 359, 333–336.
Bourne et al.(1991) *Nature* 349, 117–127.
Duigou et al.(1991) Oncogene 6,, 1813–1824.
Duigou et al.(1990) *Mol.Cell. Biol.* 10, 2027–2034.
Riis et al.(1990) *Trends Biochem. Sci.* 15, 420–424.
Hwang et al.(1989) *J. Biol. Chem.* 264, 8304–8309.
Song et al.(1989) *Mol. Cell. Biol.* 9, 4571–4575.
Sandbaken and Culbertson (1988) *Genetics* 120, 923–934.
Toulme and Helene (1988) *Gene* 72, 51–58.
Hughes et al.(1987) *EMBO J.* 6, 4235–4239.
Mukamel et al.(1987) *Urology* 30, 318–323.
Salo et al.(1987) *J. Urol.* 137, 435–438.
Tapio and Kurland (1986) *Mol. Gen. Genet.* 205, 186–188.
Babiss et al.(1985)) *Science* 228, 1099–1101.
Fisher (1984) in *Tumor Promotion and Cocarcinogenesis In Vitro: Mechanisms of Tumor Promotion,* ed. Slaga, T. J. (CRC, Boca Ration, FL), pp. 57–123.
Fisher et al.(1979) *Cell 18,* 695–705.

* cited by examiner

REVERSAL OF CANCER PHENOTYPE BY INHIBITING EXPRESSION OF PROSTATE TUMOR INDUCING GENE

This application is a Continuation application of PCT international Application No. PCT/US 97/15306, filed Sep. 5, 1997, which is a continuation-in-part of U.S. Ser. No. 08/708,206, filed Sep. 6, 1996, now abandoned, the content of which is incorporated into this application by reference.

The invention disclosed herein was made with Government support under Grant No. NIH CA 35675. Accordingly, the U.S. Government has certain rights in this invention.

BACKGROUND OF THE INVENTION

Cancer of the prostate is a major clinical problem with the diagnosis of 244,000 new cases and more than 40,500 deaths of American men predicted by the American Cancer Society in 1995. Currently, the predicted lifetime incidence of prostate cancer is 15% and the estimated lifetime death risk from this disease is approximately 3.4%. It is not possible by present technologies to distinguish between cancers that will become clinically aggressive versus indolent cancers that will remain clinically benign. Current treatment protocols, including hormonal therapy, radiation therapy and surgery have limitations. Hormonal therapy requires a hormone-responsive tumor; when a tumor develops hormone-insensitivity it can progress unchecked. Attempts at cure using radiation therapy and surgery are limited to eradication of the primary tumors. However, tumor can escape surgical or radiotherapeutic ablation, and these approaches cannot be used to successfully cure, and rarely even to limit metastatic disease. In addition, even when successful, these approaches can significantly diminish the patient's quality of life. These findings emphasize the need for improved diagnostic and therapeutic approaches for identifying prostate carcinomas, predicting clinical aggressiveness and effectively treating patients with this cancer.

Identifying the genetic elements mediating prostate cancer development and progression will lead to improved diagnostic tests and may ultimately result in gene-, immunological- and drug-based technologies with therapeutic applications. Transfection of human prostate carcinoma (LNCaP) DNA into a new DNA acceptor cell line, CREF-Trans 6, and injection into nude mice results in tumor formation (Su et al., Anticancer Res. 12:297–304, 1992). Using tumor-derived CREF-Trans 6 cells and differential RNA display, the new putative oncogene, prostate tumor inducing gene-1 (PTI-1), has been identified (Shen et al., PNAS 92: 6788–6782, 1995). PTI-1 encodes a mutated and truncated human elongation factor-1α (EF-1α). Normal EF-1α plays a prominent role in protein translation, a process that is critical in controlling gene expression and regulating cell growth. PTI-1 expression is observed in human prostate cancer cell lines (LNCaP, DU-145 and PC-3) and patient-derived prostate carcinoma tissue samples (14 of 15), but not in normal prostate (6) or BPH (4) tissue. This observation suggests that PTI-1 expression may be related specifically to carcinoma development. In addition, the observation that PTI-1 expression also occurs in a high proportion of carcinoma cell lines of the breast, colon and lung indicates that this genetic alteration may be a common event in carcinogenesis. If the modified EF-1α protein encoded by PTI-1 inhibits the ability of normal EF-1α to proofread mistakes in gene expression that mediate altered protein structure, then PTI-1 may function as a major contributor to the mutator phenotype in specific human cancers. This putative aberrant processing resulting from PTI-1 expression has been termed "translational infidelity". If this hypothesis is validated experimentally, altered protein translation would represent a new and novel mechanism underlying cancer development and progression.

Targeted inhibition of PTI-1, using genetic and/or drug interventional approaches, might therefore provide the basis for a novel strategy for the therapy of prostate cancer.

SUMMARY OF THE INVENTION

This invention provides a method for reversing cancer phenotype of a cancer cell which comprises introducing a molecule capable of specifically recognizing a Prostate Tumor Inducing Gene into the cell under conditions permitting inhibition of the expression of said gene so as to thereby reverse the cancer phenotype of the cell.

This invention also provides a method for reversing cancer phenotype of a cancer cell in a subject which comprises introducing a molecule capable of specifically recognizing a Prostate Tumor Inducing Gene into the subject's cancer cell under conditions permitting inhibition of the expression of said gene in the subject's cell so as to thereby reverse the cancer phenotype of the cell.

This invention provides a method for reversing cancer phenotype of a cancer cell which comprises introducing a compound capable of specifically recognizing the RNA of a Prostate Tumor Inducing Gene into the cell under conditions permitting inhibition of the expression of said RNA so as to thereby reverse the cancer phenotype of the cell.

This invention also provides a method for reversing cancer phenotype of a cancer cell in a subject which comprises introducing a compound capable of specifically recognizing the RNA of a Prostate Tumor Inducing Gene into the subject's cancer cell under conditions permitting inhibition of the expression of said RNA in the subject's cell so as to thereby reverse the cancer phenotype of the cell.

This invention provides a method for reversing cancer phenotype of a cancer cell which comprises introducing a substance capable of specifically recognizing the gene product of a Prostate Tumor Inducing Gene into the cell under conditions permitting inhibition of the function of said gene product so as to thereby reverse the cancerous phenotype of the cell.

This invention provides a method for reversing cancer phenotype of a cancer cell in a subject which comprises introducing a substance capable of specifically recognizing the gene product of a Prostate Tumor Inducing Gene into the subject's cancer cell under conditions permitting inhibition of the function of said gene product in the subject's cell so as to thereby reverse the cancer phenotype of the cell.

Cell types:

1A CREF-Trans 6 (parental cell line, does not express PTI-1);

1B CREF-Trans 6:4 NMT (nude mouse tumor-derived clone of CREF-Trans 6 cells transfected with high molecular weight LNCaP human prostate cancer DNA, expresses PTI-1);

1C 4NMT-Vector (Zeocin resistant CREF-Trans 6:4 NMT clone transfected with pZeoSV vector DNA);

1D 4NMT-PTI-1-AS cl 8 (flat variant of CREF-Trans 6:4 NMT cells transfected with pZeoSV containing AS PTI-1).

Figure 1A:
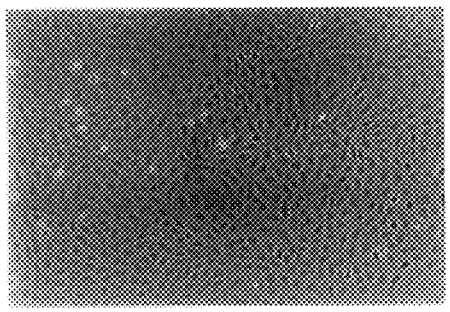
FIGS. 1A–1D. Stable expression of PTI-1 antisense reverses morphological transformation. Stable transfection of CREF-Trans 6:4 NMT cells with a pZeoSV construct (mediating resistance to Zeocin) containing the complete PTI-1 cDNA in an antisense orientation (pZeoSV-PTI-1-AS) results in colonies with a reverted flat morphology.
Figure 1B:
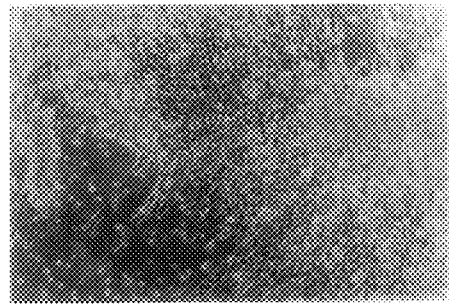
Figure 1C:
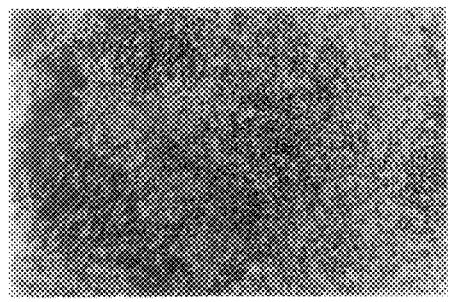
Figure 1D:
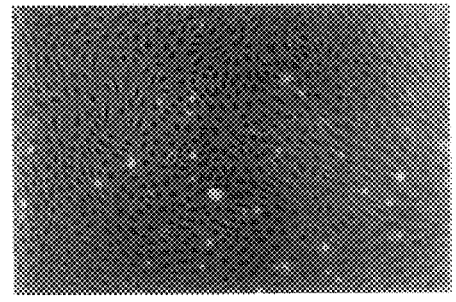
Figure 2:
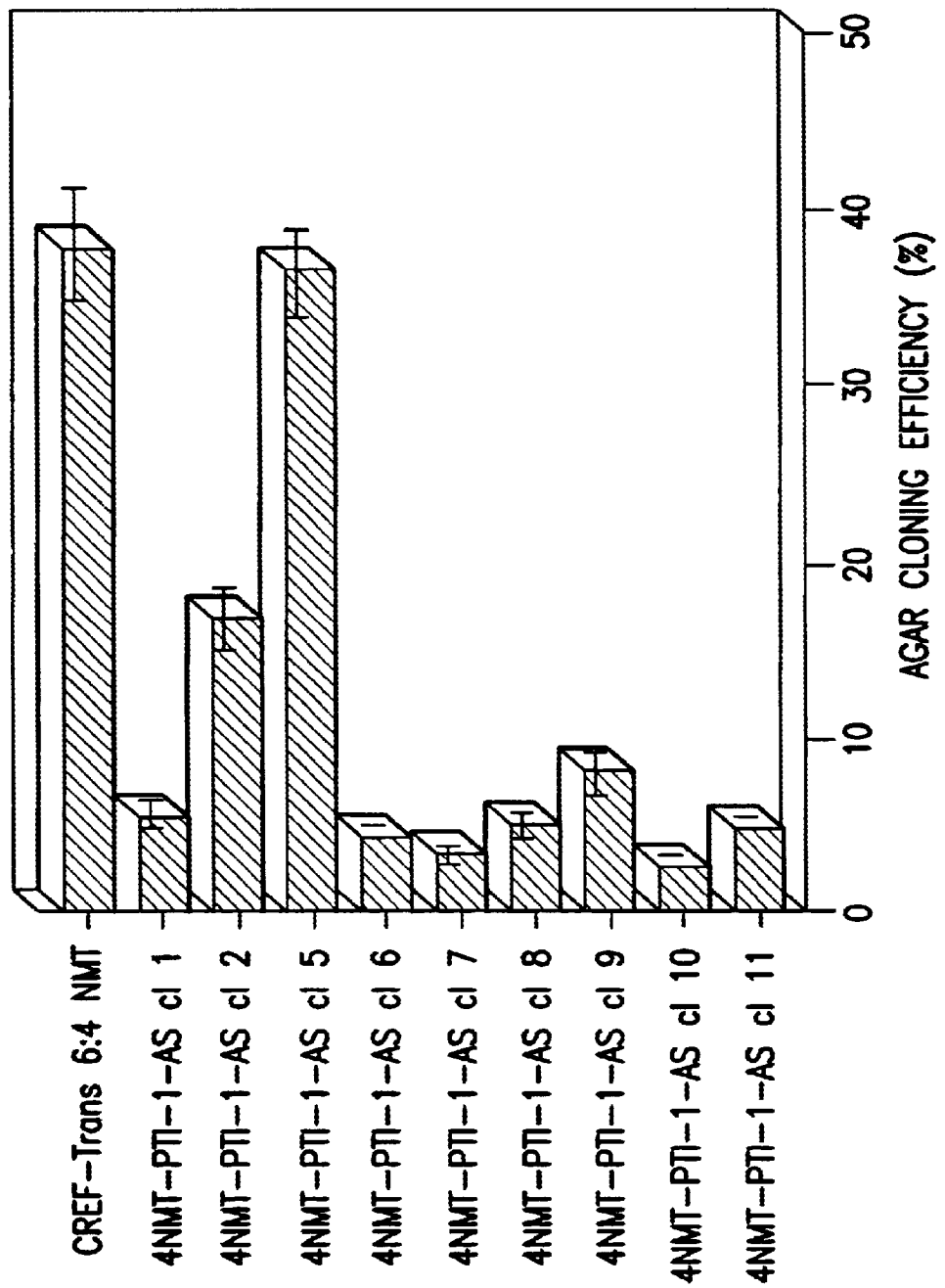

FIG. 2. Stable expression of PTI-1 antisense suppresses anchorage independent growth. A series of independent clones of CREF-Trans 6:4 NMT cells transfected with a pZeoSV construct containing the complete PTI-1 cDNA in an antisense orientation. A total of $1 \times 10^5$ cells in medium containing 0.4% Noble agar was seeded on an agar medium containing 0.8% agar. Colonies were enumerated using an inverted tissue culture microscope after 21 days. The results are the average from 4 plates±standard deviation from the mean. Cell types: CREF-Trans 6:4 NMT; 4NMT-PTI-1-AS cl 1; 4NMT-PTI-1-AS cl 2; 4NMT-PTI-1-AS cl 5; 4NMT-PTI-1-AS cl 6; 4NMT-PTI-1-AS cl 7;4NMT-PTI-1-AS cl 8; 4NMT-PTI-1-AS cl 9;4NMT-PTI-1-AS cl 10; and 4NMT-PTI-I-AS cl 11. CREF-Trans 6 cells did not form colonies in agar (data not shown).

Figure 3A:
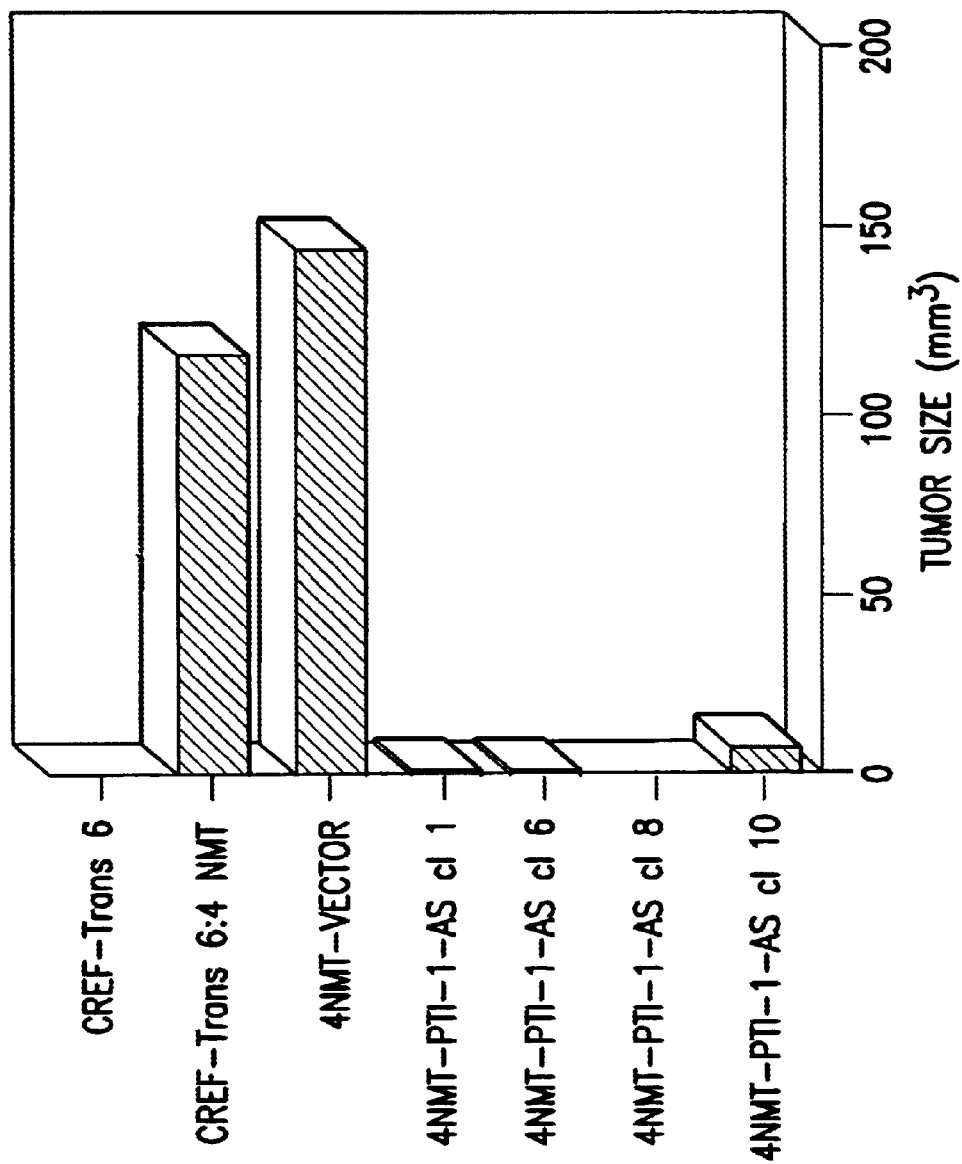
Figure 3B:
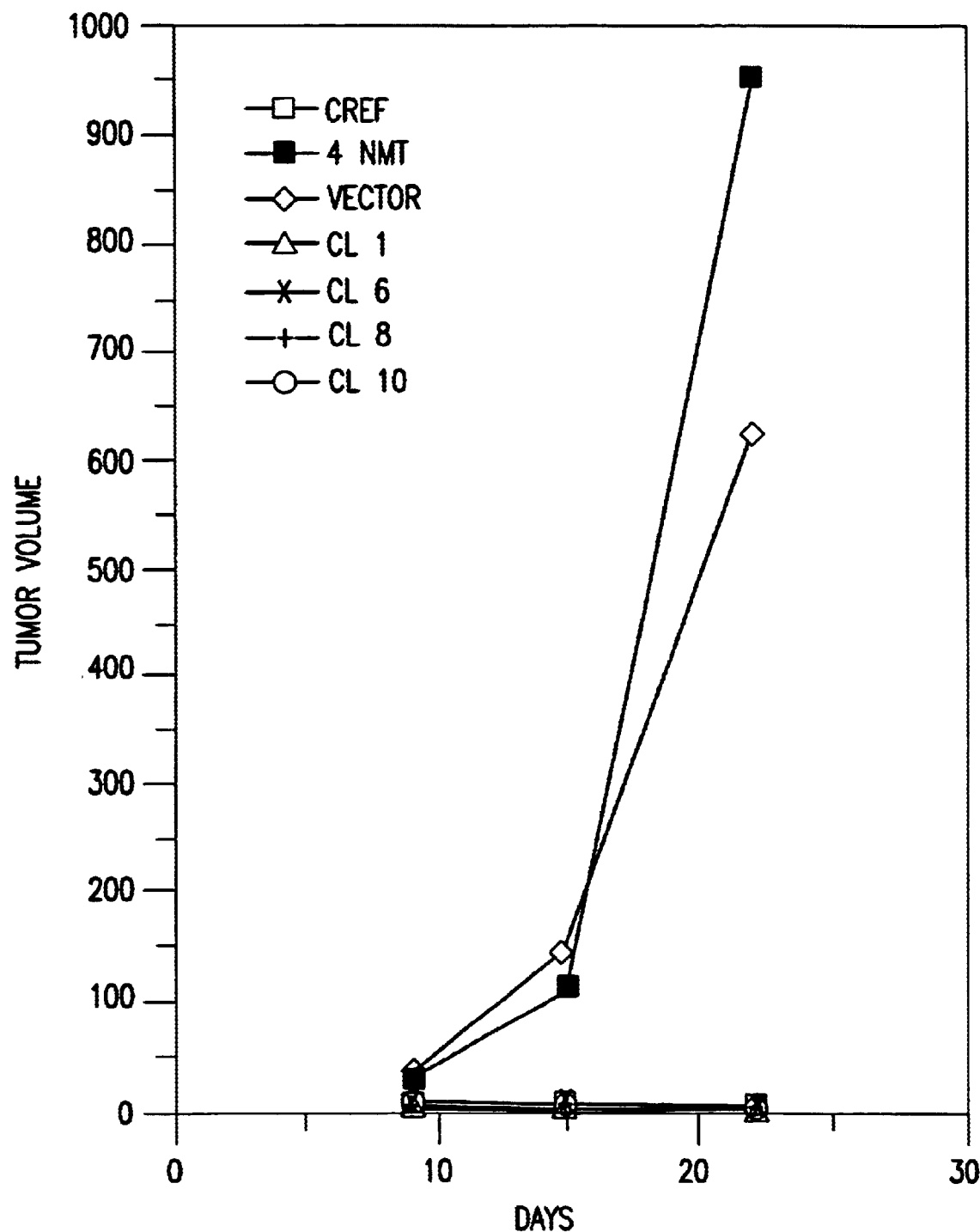

FIGS. 3A–3B. Stable expression of PTI-1 antisense suppresses tumorigenesis. Confluent cultures were resuspended using trypsin-versene. Cells were washed twice with serum free medium and viable cell counts determined using the trypan blue dye exclusion technique. Cells were resuspended in serum free medium at a concentration of $1 \times 10^7$ cells/ml and 0.2 ml was injected subcutaneously into nude mice (Balb/c nu/nu, Taconic; 5 animals per cell line.) Animals were monitored daily for tumor growth and tumors were measured once a week with a caliper. Tumor volume was derived from the formula: $\pi/6 \times \text{larger diameter} \times (\text{smaller diameter})^2$. Cell types: CREF-Trans 6 (CREF); CREF-Trans 6:4 NMT (4 NMT); 4NMT-Vector (Vector); 4NMT-PTI-1-AS cl 1 (cl 1); 4NMT-PTI-1-AS cl 6 (cl 6); 4NMT-PTI-1-AS cl 8 (cl 8); and 4NMT-PTI-1-AS cl 10 (cl 10).

3A: Tumor data evaluated at the 14 day;

3B: Tumor data evaluated at the 21 day.

Figure 4A:
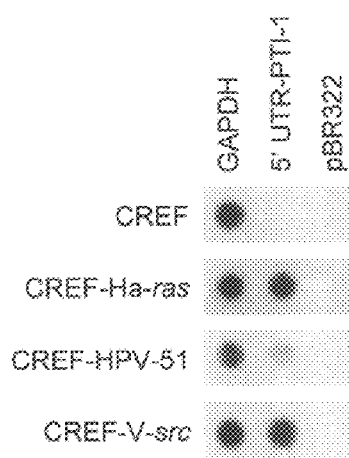
Figure 4B:
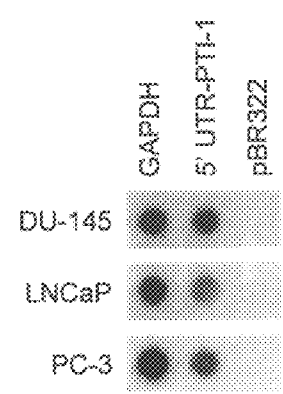
Figure 4C:
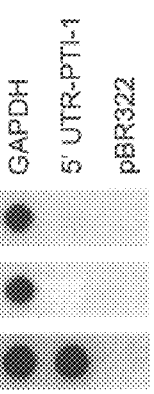

FIGS. 4A–4C. Transcription of the 5' untranslated region (5' UTR) of PTI-1 occurs following induction of oncogenic transformation in rodent cells and in specific human cancer cells. Nuclei from $2 \times 10^6$ cells were isolated form each of the cell lines shown and nuclear RNA was labeled in vitro and subsequently hybridized to denatured DNA probes on nitrocellulose filters. For each hybridization reaction, an equal number of total counts representing a similar number of nuclei was used, so that comparative rates of transcription could be obtained. Cell line designation:

4A: CREF (cloned rat embryo fibroblast); CREF-Ha-ras (CREF cells transformed by the Ha-ras oncogene); CREF-HPV-51 (CREF cells transformed by the E6/E7 transforming region of human papilloma virus-51; CREF-v-src (CREF cells transformed by the v-src oncogene)

4B: DU-145 (hormone refractive human prostate carcinoma cell line); LNCaP (hormone responsive human prostate carcinoma cell line); PC-3 (hormone retractive human prostate carcinoma cell line);

4C: HO-1 (human melanoma cell line); MCF-7 (human breast carcinoma cell line); T47D (human breast carcinoma cell line). The gene probes utilized were: GAPDH (glyceraldehyde phosphate dehydrogenase); 5' UTR PTI-1 (5' untranslated region of PTI-1): pBR322 (bacterial DNA sequences)

Figure 5:
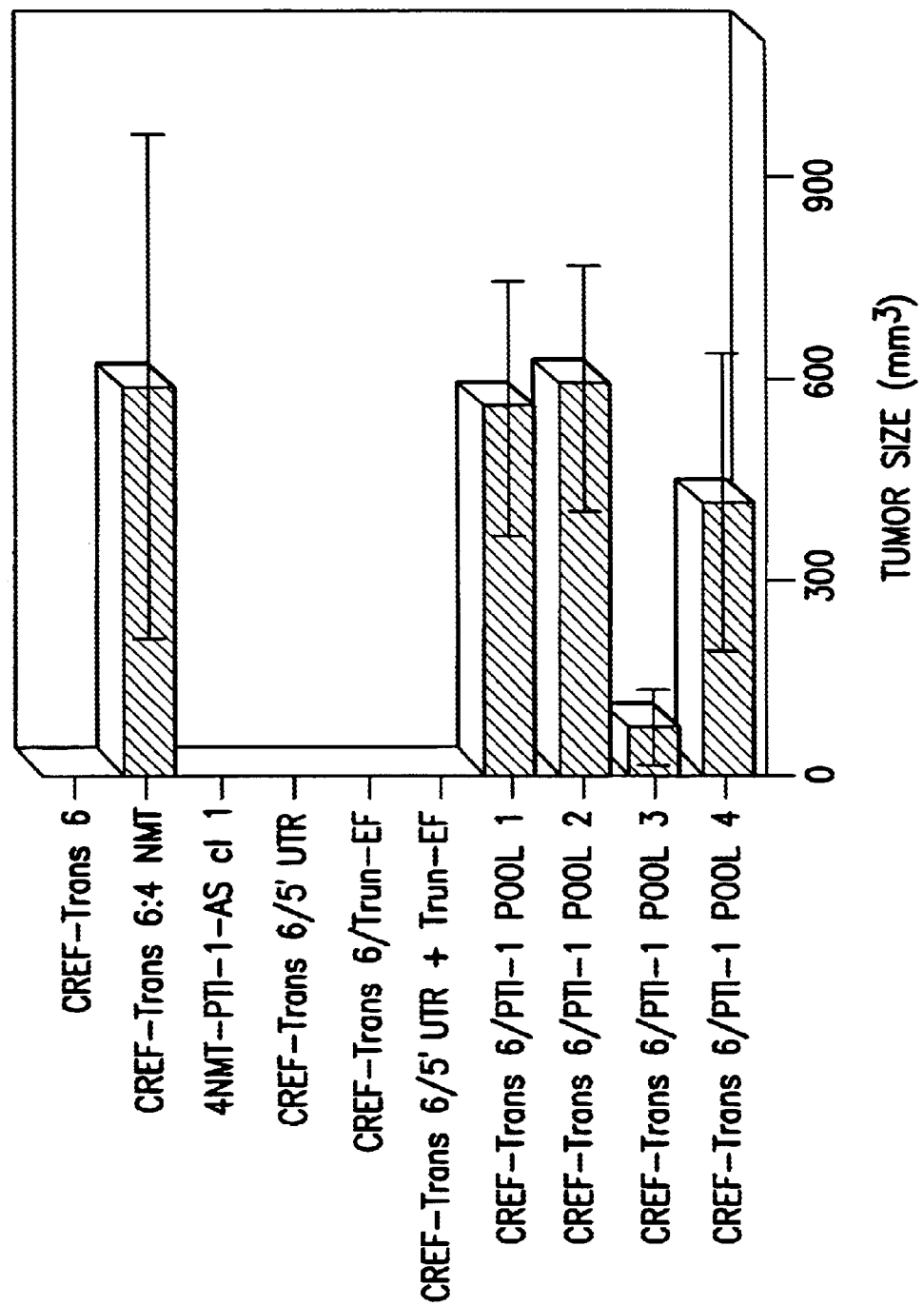

FIG. 5. Induction of tumors in nude mice by PTI-1. Pooled zeocin resistant CREF-Trans 6 cells transfected with a pZeoSV vector or a 1.9 kb PTI-1 S cDNA, a 5' UTR PTI-1 S DNA or a Trun-EF PTI-1 S DNA cloned into a pZeoSV vector were injected at $1 \times 10^6$ cells per nude mouse (n=4). Animals were also injected with untransfected CREF-Trans 6 cells, CREF-Trans 6:4 NMT cells (NMT; tumor-derived CREF-Trans 6 cells transfected with LNCaP high molecular weight DNA) and pooled CREF-Trans 6 cells transfected with the combination of a separate 5' UTR PTI-1 S and a Trun-EF S DNA cloned into pZeoSV vectors. Tumors developed in the majority of 1.9 kb PTI-1 S cDNA and 4NMT injected animals by 7 days, and in all 1.9 kb PTI-1 S cDNA and 4NMT injected animals by 10 days.

Figure 6:
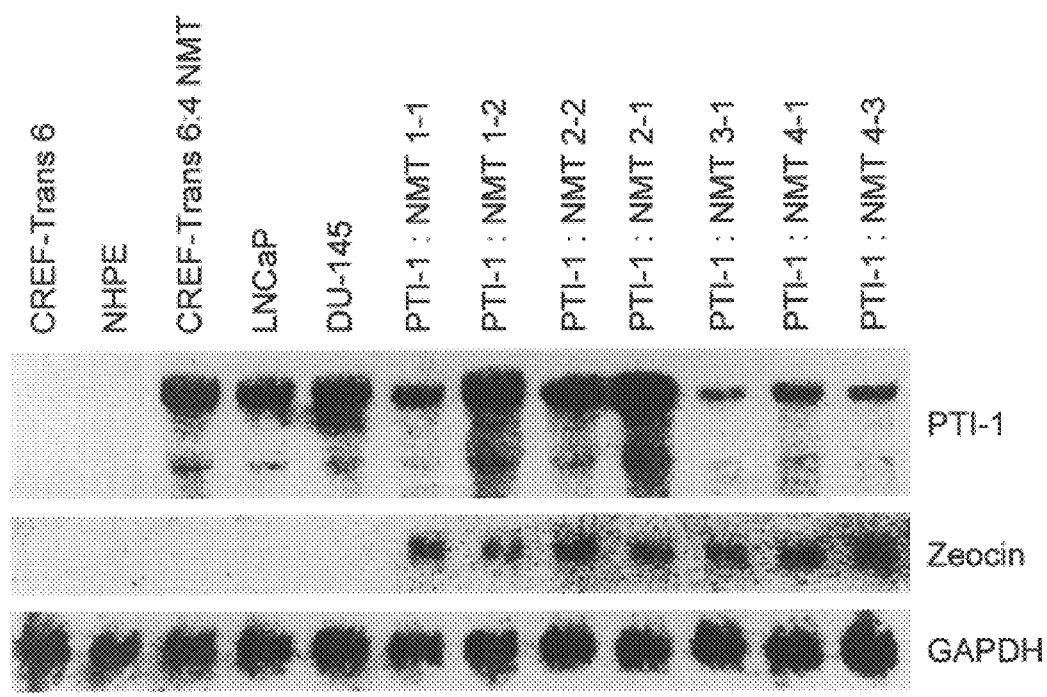

FIG. 6. Expression of PTI-1 in nude mouse tumor-derived CREF-Trans 6 cells. Tumors were isolated from animals, established in culture in the presence of zeocin, total RNA was isolated and analyzed by Northern blotting. Northern blots were sequentially hybridized with a PTI-1, zeocin and then a GAPDH cDNA probe. NHPE, normal human prostate epithelial cells; PTI-1 NMT 1-1, 1-2, 2-2, 2-1, 3-1, 4-1 and 4-3 represent independent tumors isolated from different animals.

Figure 7:
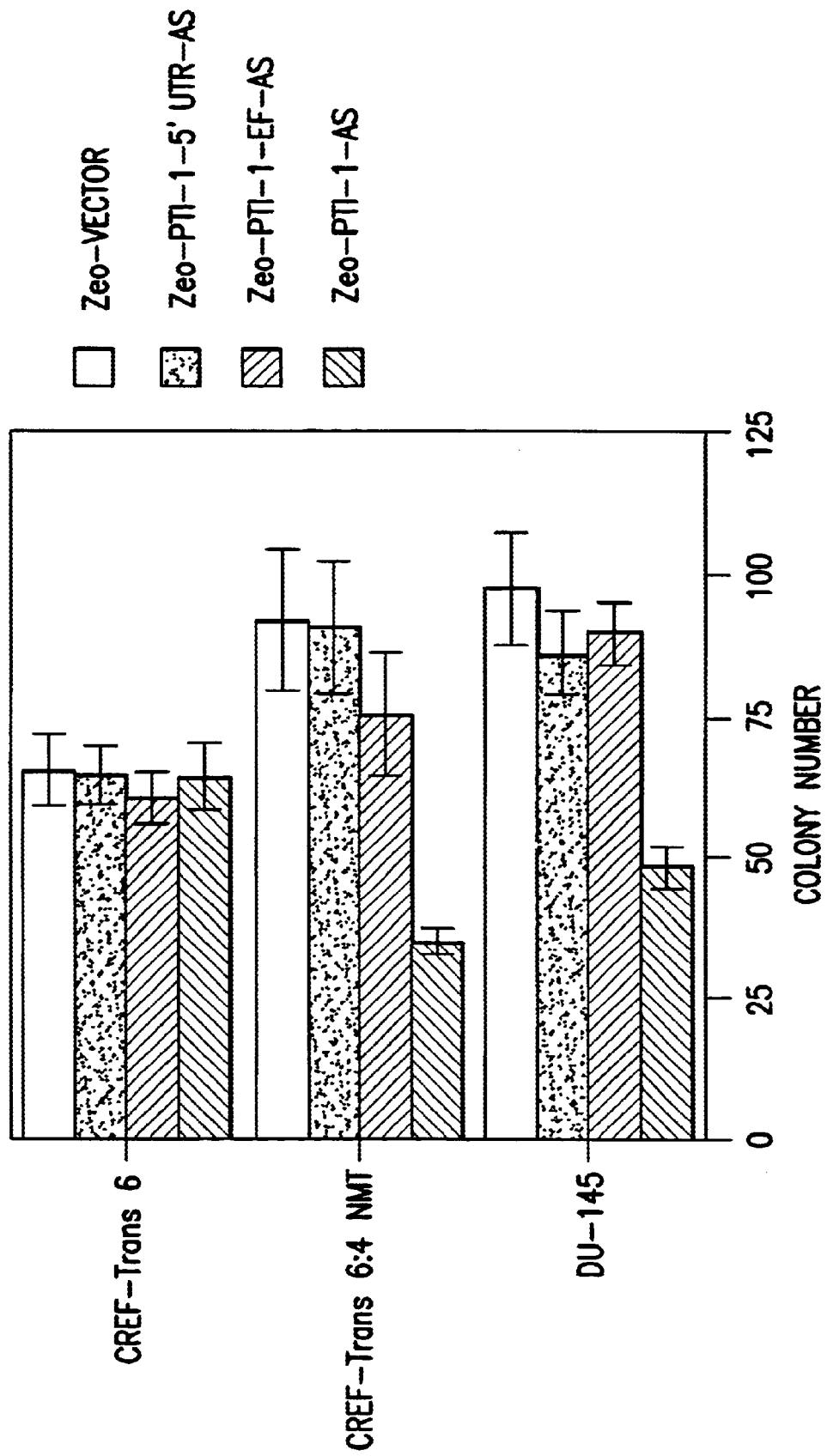

FIG. 7. Inhibition of colony formation in PTI-1 expressing cells by antisense PT1-1. The indicated cell line was transfected with a pZeoSV plasmid containing or lacking an AS 0 to 500 PTI-1 5' UTR, an AS Trun-EF region of PTI-1 or an AS PTI-1 1.9 kb sequence. Transfected cells were selected in zeocin and colony formation was determined. Results are the mean using 4 test plates per experimental condition±S.D. Similar results were obtained±10% in 2 additional experiments.

Figure 8A:
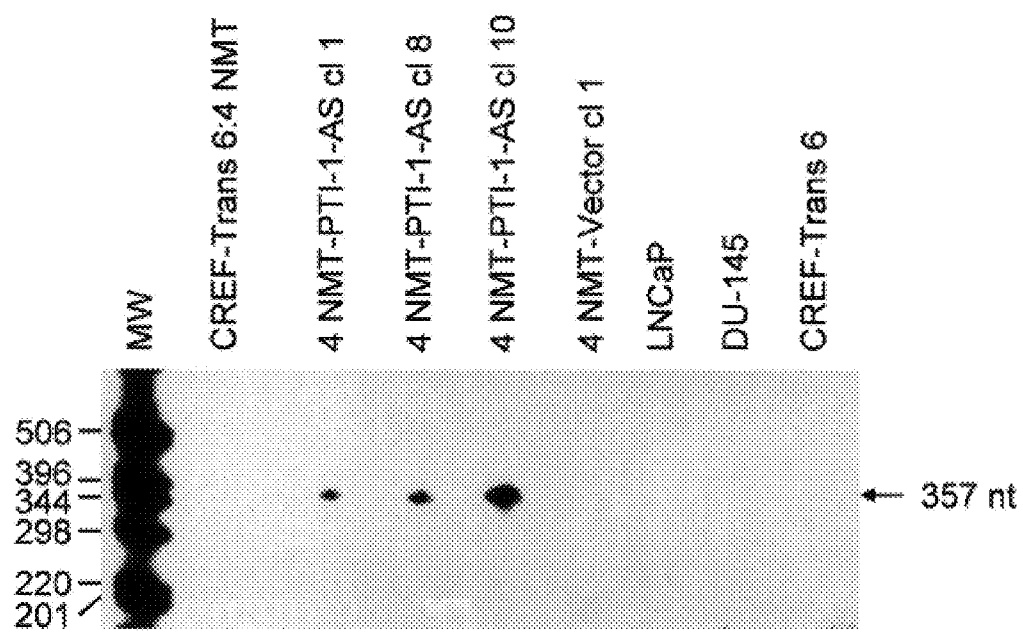
Figure 8B:
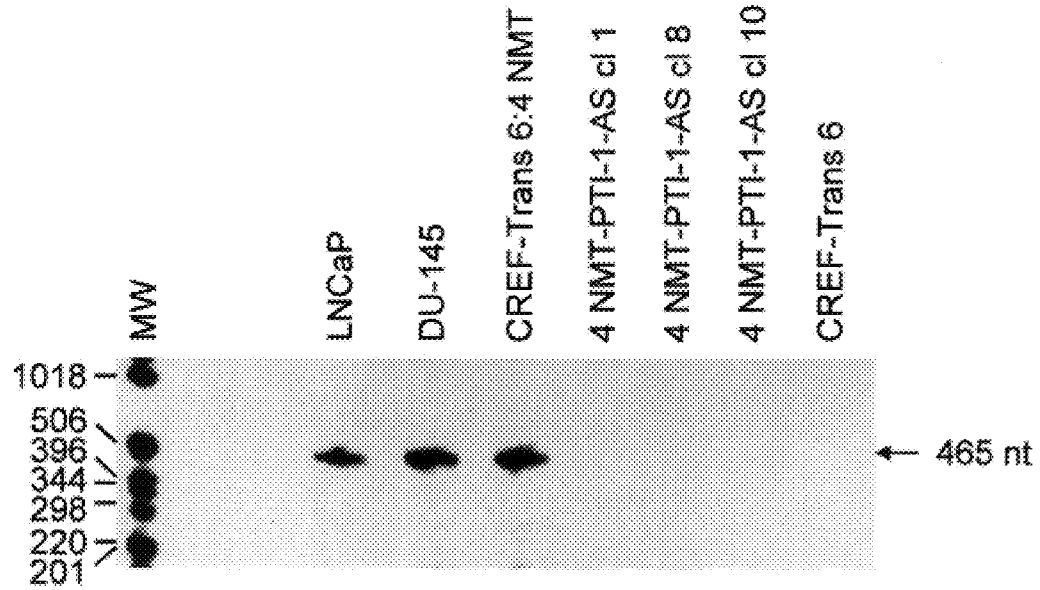
Figure 8C:
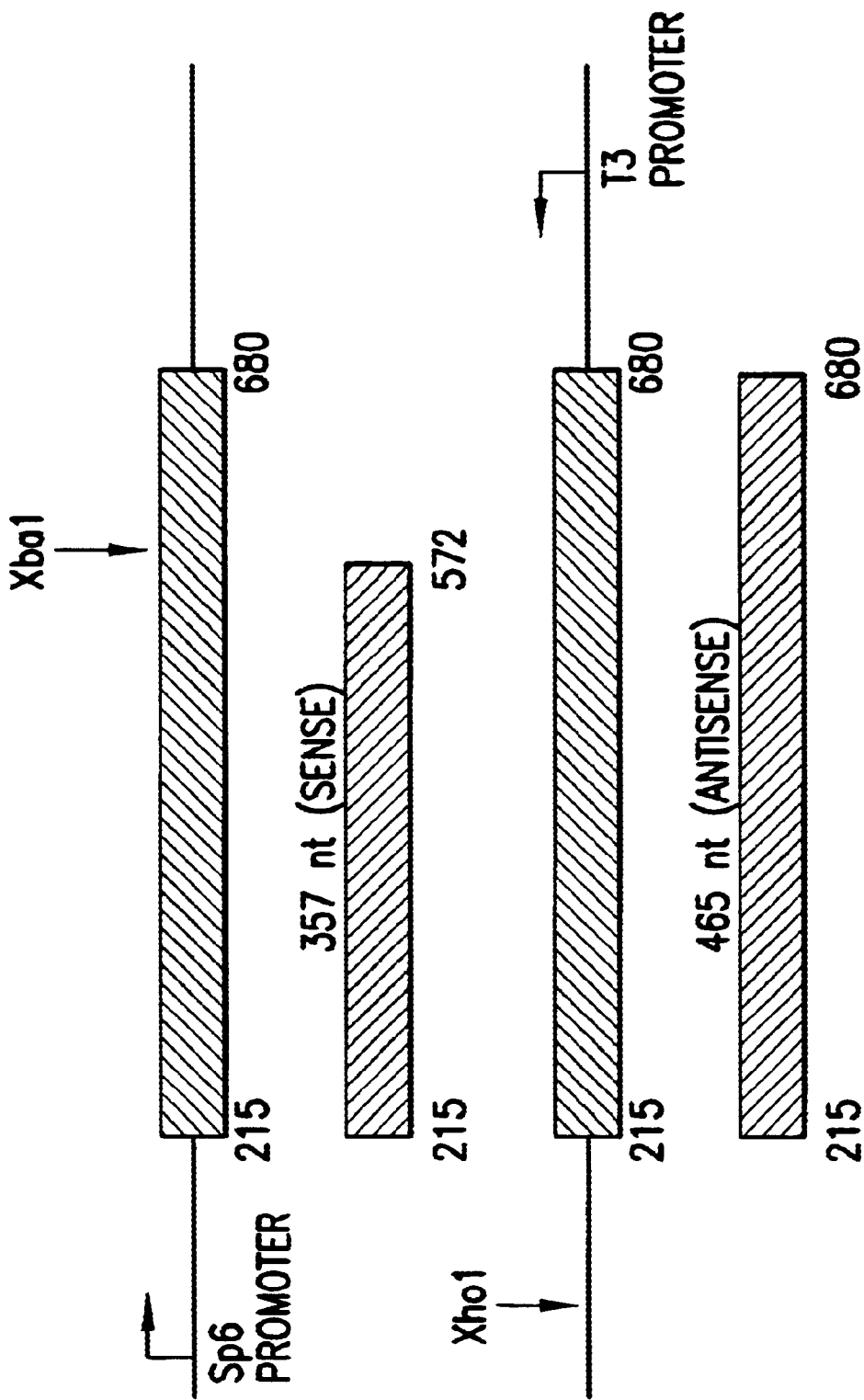

FIGS. 8A–8C. Expression of AS PTI-1 and the absence of S PTI-1 in morphologically reverted PTI-1 AS CREF-Trans 6:4 NMT clones. RNase protection assays using a 357 nt S PTI-1 probe demonstrate the presence of PTI-1 AS transcripts in phenotypically reverted 4 NMT-PTI-1-AS expressing CREF-Trans 6:4 NMT clones. RNase protection assays using a 465 nt AS PTI-1 probe demonstrate the absence of PTI-1 S transcripts in phenotypically reverted 4 NMT-PTI-1-AS expressing CREF-Trans 6:4 NMT clones.

Figure 9:
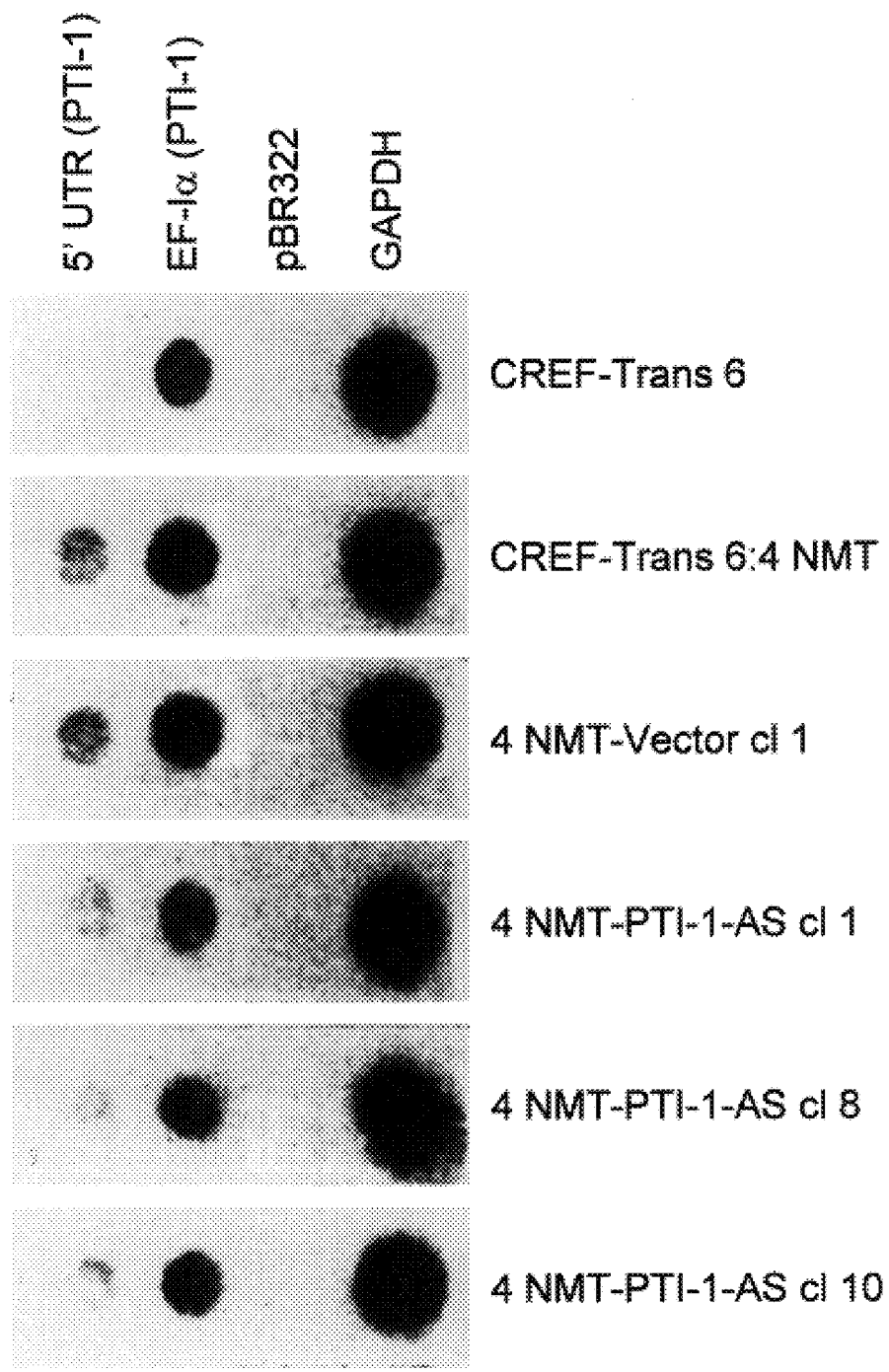

FIG. 9. Transcription of the 5' UTR of PTI-1, EF-1α and GAPDH in CREF-Trans 6:4 NMT, 4NMT-Vector and 4NMT-PTI-1-AS cells. Nuclear run-on assays were performed using the indicated cell types. DNA probes immobilized on filters include 5' UTR (0 to 500 bp region of PTI-1), Trun-EF (EF-1α isolated from PTI-1), pBR322 and GAPDH.

DETAILED DESCRIPTION OF THE INVENTION

This invention provides a method for reversing cancer phenotype of a cancer cell which comprises introducing a molecule capable of specifically recognizing a Prostate Tumor Inducing Gene into the cell under conditions permitting inhibition of the expression of said gene so as to thereby reverse the cancerous phenotype of the cell.

This invention also provides a method for reversing cancer phenotype of a cancer cell in a subject which comprises introducing a molecule capable of specifically recognizing a Prostate Tumor Inducing Gene into the subject's cancer cell under conditions permitting inhibition of the expression of said gene in the subject's cell so as to thereby reverse the cancerous phenotype of the cell.

This invention provides a method for reversing cancer phenotype of a cancer cell which comprises introducing a compound capable of specifically recognizing the RNA of a Prostate Tumor Inducing Gene into the cell under conditions permitting inhibition of the expression of said RNA so as to thereby reverse the cancerous phenotype of the cell.

This invention also provides a method for reversing cancer phenotype of a cancer cell in a subject which comprises introducing a compound capable of specifically recognizing the RNA of a Prostate Tumor Inducing Gene into the subject's cancer cell under conditions permitting inhibition of the expression of said RNA in the subject's cell so as to thereby reverse the cancerous phenotype of the cell.

This invention provides a method for reversing cancer phenotype of a cancer cell which comprises introducing a substance capable of specifically recognizing the gene product of a Prostate Tumor Inducing Gene into the cell under conditions permitting inhibition of the function of said gene product so as to thereby reverse the cancerous phenotype of the cell.

This invention provides a method for reversing cancer phenotype of a cancer cell in a subject which comprises introducing a substance capable of specifically recognizing the gene product of a Prostate Tumor Inducing Gene into the subject's cancer cell under conditions permitting inhibition of the function of said gene product in the subject's cell so as to thereby reverse the cancerous phenotype of the cell.

In an embodiment of the above methods, the cancer cell is a prostate cancer cell, a breast cancer cell, a colon cancer cell, or a lung cancer cell.

In another embodiment of the above methods, the Prostate Tumor Inducing Gene is PTI-1, PTI-2 or PTI-3. PTI-1, -2 and -3 are described in copending U.S. Ser. No. 08/371,377, filed Jan. 11, 1995 and Patent Cooperation Treaty Application No. PCT/US96/00307, filed Jan. 1996.

PTI-1 and Prostate Tumor Inducing Gene-2 (PTI-2): A cDNA library was prepared from LNCaP cells in the Uni-ZAP XR vector (Stratagene). The LNCaP cDNA library was screened with a $^{32}$P-labeled 1.8 Kb DNA (PTI-3) containing the 214 bp DNA obtained by the differential display procedure. The contents of ten plates of 150 mm×15 mm (containing ~2×10$^4$ plaques/plate) were transferred in duplicate to nylon membranes. Hybridization was performed using the following conditions: 5% dextran sulfate, 45% deionized formamide, 4×SSC, 1 mM phosphate buffer (pH 7.5), 0.5% SDS, 5% Denhardt's reagent at 42° C. in a Hybridization Incubator Model 400 (Robbin Scientific); washing at 55° C. for 60 mm in a solution of 0.25% SDS and 1×SSC. Positive plaques obtained in the first round were screened in duplicate for a second round and then with in vivo excision produced plasmids containing gene inserts in the pBluescript vector. Plasmids containing the longest inserts were identified by Southern blotting and probing with the 1.8 Kb (PTI-3) DNA probe. Two clones were identified using this approach: clone 8 (PTI-2) and clone 18 (partial sequence of PTI-1)

The full sequence of PTI-1 contains 2,123 bp, the 5'-flanking (1-215 bp) was obtained by RACE 5'-extension (CIBCO-BRL), the remaining 216–2,123 bp was obtained by sequencing clone 18. The RACE 5' extension was performed with two oligonucleotides, both located within the 5'-end of clone 18. One oligonucleotide is a 23 mer (5'-CCTTGCATATTAACATAACTCGC-3') and the other oligonucleotide is a 20 mer (5'-AAGTCGCCCTATTCAGACTC-3'). A comparison of PTI-1 with GenBank indicates that the 3'-part of this gene (630 to 2,123 bp) has 97% homology to human elongation factor 1-alpha. The 5'-part of this gene (1–629 bp) does not show any homology to known eucaryotic genes.

Comparison of PTI-2 with Cenbank indicates that it has 86.9% identity in 1356 bp overlap with *Mycoplasma floccular* 16S ribosomal RNA and 23S ribosomal RNA genes, but no homology to any previously identified eucaryotic genes.

Prostate Tumor Inducing Gene-3 (PTI-3): To identify genes specifically expressed in CREF-Trans 6:4 NMT (transformed by DNA from LNCaP cells), but not CREF-Trans 6 cells applicants have used the differential RNA display procedure. This approach resulted in the identification of a 214 bp DNA fragment in CREF-Trans 6:4 NMT that was not present in CREF-Trans 6 cells (PNAS paper). Northern blotting indicates that this 214 bp DNA is expressed in CREF-Trans 6:4 NMT and LNCaP cells, but not in CREF-Trans 6 cells. A 20 mer oligonucleotide with the sequence 5'-AACTAACTGGAGGACCGAAC3' within this 214 bp DNA fragment was used to obtain extended sequences beyond the 214 bp DNA using the RACE method. A cDNA from LNCaP cells was synthesized with oligodT. To the 3'-end a polydC was added by terminal deoxynucleotide transferase. When the anchor primer (using the protocol of the GIBCO-BRL 5' RACE kit) and the above 20 mer were used to perform POR amplification of cDNA from LNCaP cells, a 1.8 Kb DNA fragment containing a partial sequence of the 214 bp DNA was obtained. This 1.8 Kb DNA fragment displays the same Northern blotting pattern as does the unique 214 bp sequence.

The 1.8 Kb DNA fragment was cloned into PCR™ II vector by using the TA cloning kit (Invitrogen). The sequence of this 1.8 Kb DNA was determined by Sanger's method (Sequenase kit, version 2.0 USB) The 1.8 Kb DNA contains a partial sequence of PTI-1/3. The 5' and 3' end of PTI-3 gene remains to be confirmed. The insert of PTI-3 1.8 Kb insert can be recovered from the PCR™TI vector by digestion with EcoRI. A comparison of the sequence of PTI-3 with Genbank data base indicates that this gene has 87% identity in 1858 bp overlap with *Mycoplasma floccular* 16S ribosomal RNA and 23S ribosomal RNA genes, and it has 89.8% identity in 1858 bp overlap with *Mycobacterium hyopneumoniae* 23S ribosomal RNA gene.

In an embodiment, the molecule capable of specifically recognizing a Prostate Tumor Inducing Gene is a nucleic acid molecule. In another embodiment, the compound capable of specifically recognizing the RNA of a Prostate Tumor Inducing Gene is a nucleic acid molecule. These nucleic acid molecules may be a ribozyme. These nucleic acid molecule may comprise an expression vector. Specifically, these nucleic acid molecule may have sequence complementary to the unique region of the Prostate Tumor Inducing Gene. Such region may be the 5 prime or the 3 prime untranslated region of the PTIs. These nucleic acid molecules may also be complementary to the untranslated region of the PTIs.

In another embodiment, the nucleic acid molecule is complementary to the 5' untranslated region and the EF-1α region of the said gene. In a further embodiment, the nucleic acid molecule comprises the sequence of 5'AAATTAAGC-TATGCAGTCGG3' (SEQ ID NO:1.

In a further embodiment, the nucleic acid comprises a vector. The vector includes, but is not limited to, an adenovirus vector, adeno-associated virus vector, Epstein-Barr virus vector, Herpes virus vector, attenuated HIV virus, retrovirus vector and vaccinia virus vector.

Methods to introduce a nucleic acid molecule into cells have been well known in the art. Naked nucleic acid molecule may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, mechanical or electrical means. The above recited methods are merely served as examples for feasible means of introduction of the nucleic acid into cells. Other methods known may be also be used in this invention.

In another embodiment, the substance capable of specifically recognizing the gene product of a Prostate Tumor Inducing Gene is an antibody which specifically binds to the protein of a Prostate Tumor Inducing Gene.

This invention provides a method for killing a cancer cell which comprises introducing the promoter of a Prostate Tumor Inducing Gene operatively linked to nucleic acid having sequence which encodes at least one toxic factor into the cell under conditions permitting expression of said toxic factor so as to thereby kill the cancer cell.

This invention also provides a method for killing a cancer cell in a subject which comprises introducing the promoter of a Prostate Tumor Inducing Gene operatively linked to nucleic acid having sequence which encodes at least one toxic factor into the subject's cancer cell under conditions permitting expression of said toxic factor in the subject's cell so as to thereby kill the cancer cell.

This invention provides a pharmaceutical composition which comprises an amount of a molecule capable of specifically recognizing a Prostate Tumor Inducing Gene effective to inhibit the expression of the Prostate Tumor Inducing Gene, thereby reversing the cancer phenotype of a cancer cell and a pharmaceutically acceptable carrier.

As used herein, the term "pharmaceutically acceptable carrier" encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention provides a pharmaceutical composition which comprises an amount of a compound capable of specifically recognizing the RNA of a Prostate Tumor Inducing Gene effective to inhibit the expression of the RNA of the said gene, thereby reversing the cancer phenotype of a cancer cell and a pharmaceutically acceptable carrier.

This invention provides a pharmaceutical composition which comprises an amount of a substance capable of specifically recognizing the gene product of a Prostate Tumor Inducing Gene effective to inhibit the function of such gene product, thereby reversing the cancer phenotype of a cancer cell and a pharmaceutically acceptable carrier.

This invention also provides a pharmaceutical composition comprising an amount of a nucleic acid molecule which is complementary to a Prostate Tumor Inducing Gene effective to inhibit the expression of said gene and a pharmaceutically acceptable carrier.

This invention provides a pharmaceutical composition comprising an amount of a nucleic acid molecule which is complementary to the 5' untranslated region and the EF-1α region of a Prostate Tumor Inducing Gene effective to inhibit the expression of said gene and a pharmaceutically acceptable carrier. In an embodiment of the pharmaceutical composition, the nucleic acid molecule comprises the sequence of 5'AAATTAAGCTATGCAGTCGG3'.

This invention provides the above pharmaceutical composition, wherein the cancer cell is a prostate cancer cell, a breast cancer cell, a colon cancer cell, or a lung cancer cell.

Finally, this invention provides a method for reversing cancer phenotype of a cancer cell in a subject which comprises administering the above pharmaceutical composition into the subject so as to reverse the cancer phenotype of the cell.

This invention will be better understood from the Experimental Details which follow. However, one skilled in the art will readily appreciate that the specific methods and results discussed are merely illustrative of the invention as described more fully in the claims which follow thereafter.

Experimental Details

The ability of PTI-1 to discriminate between normal prostate, BPH and prostate carcinoma suggests that PTI-1 may prove valuable as a diagnostic and a therapeutic reagent for prostate cancer. In preliminary studies, the potential use of PTI-1 for detecting prostate carcinoma cells diluted with normal cells and the presence of metastatic prostate carcinoma cells in the peripheral circulation has been evaluated. PTI-1 expressing LNCaP cells were serially diluted with PTI-1 nonexpressing CREF-Trans 6 cells, cellular RNAs were isolated and analyzed by RT-PCR using primers specific for the unique 5' region of PTI-1. Additionally, the same RNA samples were analyzed by RT-PCR using primers specific for two well-established prostate gene products, PSA and PSM. Using this approach, PTI-1 could detect the equivalent of one LNCaP cell diluted in $10^8$ CREF-Trans 6 cells, whereas the sensitivity of PSA and PSM maximally detected one LNCaP cell diluted in $10^6$ CREF-Trans 6 cells. This finding is important since recent studies indicate that the detection of blood-borne PSA-synthesizing cells by RT-PCR can be accomplished in patients with localized as well as metastatic prostate cancer and that this detection provides a reliable marker for predicting local invasion of a prostate tumor prior to surgical procedures. In preliminary studies, several blood RNA samples from patients with metastatic disease were analyzed by RT-PCR and found to be positive for both PSA and PTI-1. The biological significance of the prostate cells in the circulation is not presently known. However, the high percentage of frank metastatic patients that give a positive reaction on this assay suggests that it is detecting circulating metastatic prostate cells. Multiple mRNA tissue Northern blots (Clontech) have now been used to determine which normal human tissue contains mRNA that hybridizes with the 5' unique region of PTI-1 and the EF-1α region of PTI-1.

These experiments indicate that the unique 5' region of PTI-1 is expressed in skeletal muscle and in colon, but not in spleen, thymus, prostate, testis, ovary, small intestine, peripheral blood, heart, brain, placenta, lung, liver, kidney or pancreas. In contrast, probing the same Northern blots with a region of the EF-1α region of PTI-1 results in expression in all of the tissues tested. PTI-1 expression has also been detected using RT-PCR in blood RNA samples from patients with metastatic disease that have also been found to be positive for PSA expression. These data, which indicate that PTI-1 is 100× more sensitive than PSA or PSM in detecting prostate carcinoma cells, that blood RNAs from patients with metastatic prostate disease are positive for both PSA and PTI-1 and that peripheral blood cells do not express PTI-1, suggest that PTI-1 may prove selective and sensitive for the early detection of prostate carcinoma cells in the peripheral circulation.

The ability of anti-sense PTI-1 (PTI-1-AS) to alter the transformed phenotype of tumor derived LNCaP DNA transfected CREF-Trans 6 (CREF-Trans 6:4 NMT) cells has been determined (FIGS. 1–3). PTI-1 was cloned in an antisense orientation (PTI-1-AS) into pZeoSV vector, that contains a cloning site adjacent to a SV40 enhancer and promoter and also contains a selectable Zeocin resistance gene controlled by a CMV promoter. Transfection of this construct into CREF-Trans 6:4 NMT followed by growth in Zeocin resulted in the identification of several Zeocin resistant colonies displaying a reverted normal CREF-Trans 6-like morphology (FIG. 1). These PTI-1-AS-reverted clones were isolated and found to exhibit a reduced ability to form colonies when seeded in agar, i.e., ~40% for parental CREF-Trans 6:4 NMT cells versus ~<10% for the different PTI-1-AS-reverted clones (FIG. 2). This observation indicates that altering PTI-1 expression may mediate a reversal in the transformed properties of PTI-1-expressing cells. When anti-sense PTI-1 expressing revertant, CREF-trans 6:4 NMT cells are injected into nude mice, tumor formation is prevented (FIGS. 3A and 3B). These exciting findings clearly warrant further studies. These include determining the effect of blocking PTI-1 expression on tumorigenic properties of CREF-Trans 6:4 NMT cells and determining the effect of PTI-1-AS expression, with phosphorothioate oligonucleotides, additional expression vector constructs and adenoviral constructs, on the in vitro and in vivo properties of human prostate cancer cells, such as LNCaP, DU-145 and PC-3 cells. The efficacy of adenoviral vectors for reversing prostate cancer by constructing vectors expressing the anti-sense RNA of PTI-1 will be important to test. The efficacy of adenovirus vectors containing a PTI-1-AS gene in reversing the in vitro transformation-related and in vivo oncogenic properties of human prostate cancer cells in nude mice xenograft experiments also requires testing. The continued success of this anti-sense approach in reversing the cancer phenotype would serve as the basis for expanded in vivo animal studies. These types of studies will be necessary as a first step in validating PTI-1-AS for therapeutic applications in males with prostate cancer.

The full-length PTI-1 cDNA is 2,123 bp and consists of a unique 630 bp 5' region and a 3' region extending from 630 to 2,123 bp that displays 97% homology to a truncated and mutated (6 point mutations) human EF-1α gene. Since PTI-1 encodes a truncated version of EF-1α, 46 kDa versus 50 kDa for wild-type human EF-1α, antibodies produced against specific regions of the EF-1α protein may prove amenable for detecting PTI-1 expression in cancer tissue. This possibility will be determined by immunoprecipitation and Western blotting analysis with peptide-derived rabbit polyclonal antibodies prepared against the N-terminus of human EF-1α (missing in the PTI-1 gene), antibodies prepared against the specific mutated regions of EF-1α present in PTI-1 and antibodies prepared against the C-terminus of human EF-1α. If carcinoma cells contain both EF-1α and PTI-1, then N-terminus antibodies should react only with the ~50 kDa EF-1α protein whereas C-terminus antibodies should react with both the ~50 kDa EF-1α and the ~46 kDa PTI-1 proteins. In this context, detection of the ~46 kDa PTI-1 protein could prove diagnostic for carcinomas.

PTI-1 also contains six point mutations in its EF-1α gene region that allows it to be distinguished from wild-type human EF-1α. At the present time, the significance of these specific point mutations in the EF-1α coding region of PTI-1 is not known. To determine the frequency of the specific mutations in EF-1α during human prostate carcinoma development the single-stranded conformation polymorphism (SSCP) technique will be used. A single nucleotide difference between two short single-stranded DNA molecules can produce a difference in the conformations sufficient to produce changes in the molecules' electrophoretic mobilities on neutral polyacrylamide gels. Using SSCP it will be possible to determine the frequency of specific mutations in the EF-1α coding region of PTI-1 in human prostate cancers. Sequence analyses will be used to confirm the mutational changes.

Preliminary experiments indicate that PTI-1 expression can be detected in RNA samples isolated from prostate carcinoma cell lines, patient-derived prostate carcinoma tissue samples and blood samples from patients with metastatic disease. These studies are being expanded using a minimum of 30 histologically confirmed samples from normal prostate (autopsy), patient-derived BPH and patient-derived prostate carcinoma. Blood RNA samples from patients with and without confirmed metastatic disease and with and without confirmed PSA and PSM expression will also be evaluated for expression of PTI-1. These studies will be necessary to statistically confirm the initial observation of differential expression of PTI-1 in human prostate carcinomas versus normal prostate and BPH and expression of PTI-1 in blood samples from patients with metastatic disease. To define the precise localization within the prostate of PTI-1 expression we will use in situ hybridization. Coexpression of PSA will be determined by immunohistochemistry. Identification of the specific cell types expressing PTI-1 in prostate tumors will permit investigation of the role PTI-1 expression plays in the neoplastic transformation and tumor progression in the prostate carcinoma. Analysis of expression in normal, benign hyperplastic and neoplastic human prostate will allow comparison of expression in intraepithelial, non-invasive neoplasms and in cancers that show histologic progression from low-grade and high-grade invasive tumors, even in a single patient. For this study both fresh frozen and paraffin-embedded tissue will be used. Serially cut tissue sections will be prepared for both in situ analyses and routine hematoxylin and eosin histologic analysis so that an accurate pathologic assessment of the prostate disease in each microscopic field can be made and appropriate correlation of tumor progression with expression data inferred. This is especially important in prostate where a single tissue section can show fields ranging from benign glands, to intraepithelial non-invasive neoplasia, to invasive cancer of low, intermediate and high grades. The Gleason's grading system will be used to assess the degree of differentiation in invasive prostate adenocarcinoma.

The above findings indicate that (1) PTI-1 expression is restricted to male neoplastic tissue, (2) PTI-1 is a more sensitive indicator than PSA or PSM for detecting prostate carcinoma cells and (3) inhibiting PTI-1 expression by using PTI-1-AS can reverse the transformation phenotype.

Second Series of Experiments

The PTI-1 gene has been identified as a putative oncogene using DNA transfection and nude mouse tumor assays. By comparing RNAs synthesized in untransfected and tumor-derived human LNCaP prostate carcinoma DNA-transfected CREF-Trans 6 cells, a novel 214-bp sequence was identified using differential RNA display that is expressed in LNCaP and LNCaP DNA-transfected tumor-derived CREF-Trans 6 cells. By screening an LNCaP cDNA library and using the 5'-RACE procedure, a full-length 2.0-kb PTI-1 cDNA was obtained. Sequence analysis indicates that the PTI-1 gene contains a 630-bp 5' sequence (with ~85% sequence homology to *Mycoplasma hyopneumoniae* 23S ribosomal RNA) and a 3' sequence homologous to a truncated and mutated form of human elongation factor 1α(EF-1α). Probing Northern blots with a DNA fragment corresponding to the 5' region of PTI-1 identifies multiple PTI-1 transcripts in RNAs from human carcinoma cell lines derived from the prostate, lung, breast and colon. By using a pair of primers recognizing a 280-bp region within the 630-bp 5' untranslated region (UTR) of PTI-1, reverse transcription-PCR detects PTI-1 expression in patient-derived prostatic carcinomas but not in normal prostate or BPH tissue. In contrast, reverse transcription-PCR detects prostate-specific antigen expression in all of the prostate tissue. These results indicate that PTI-1 may be a member of a class of oncogenes that could affect protein translation and contribute to carcinoma development in human prostate and other tissues.

Aims: To evaluate the diagnostic and therapeutic potential of a putative dominant-acting nude mouse prostatic carcinoma tumor-inducing gene, PTI-1.

A. Characterizing the PTI-1 Gene and Defining its Mode of Action

The homology between the 5' UTR of PTI-1 and bacterial ribosomal 23S RNA mandated that experiments be performed to confirm the authenticity of the PTI-1 cDNA. In particular, it was important to rule out the possibility that PTI-1 resulted from a cloning artifact or mycoplasmal contamination. To approach these questions a PCR strategy was employed using primer sequences located in the 5' UTR and in the EF-1α region of PTI-1. RNAs were isolated from cell lines previously shown to be positive by both Northern blotting and RT-PCR using probes generated within the 5' UTR region of PTI-1. Using this approach, PCR fragments of the predicted size were obtained using RNA isolated from CREF-Trans 6:4 NMT and DU-145. Sequence analysis of the PCR amplified DNAs indicated the presence of both the 5' UTR and 3' EF-1α region indicating the authenticity of the PTI-1 cDNA. Since the PTI-1 cDNA isolated directly from the LNCaP cDNA library consists of 1.8-kb, primers within the 200-bp region of the 5' UTR missing in the PTI-1 cDNA were used for PCR amplification. Using this region, amplified fragments with the appropriate size and sequence were obtained from cells found to be positive using 5' UTR sequences within the cDNA of PTI-1 and the bridge region (5' UTR and 3' EF-1α sequences) of PTI-1.

It was important to determine if the 5' UTR region of PTI-1 is present in the human genome. To address this question, genomic DNA was isolated from human kidney tissue and PCR amplification was performed using primers within the 5' UTR region of PTI-1. With this approach, a band of the appropriate size and sequence was obtained indicating that this 5' UTR sequence is part of the human genome. Similarly, analyses of DNAs isolated from different species, including bacteria, yeast, monkey, rat and human, indicate the presence of PTI-1 5' UTR sequences. The ability to utilize PTI-1 for diagnostics and therapy will depend on preferential expression in human cancers. To determine the spectrum of tissue expression, RNAs have been isolated from normal human cerebral cortex, cerebellum, liver, kidney and testis and found to be negative for PTI-1 expression.

These studies indicate: (1) PTI-1 is an authentic cDNA expressed in various human cancer cells; (2) The 5' UTR of PTI-1, with sequence homology to bacterial ribosomal 23S RNA, is found in the genome of both eukaryotes and prokaryotes; and (3) The 5' UTR of PTI-1 is not expressed in a spectrum of normal tissue.

B. Determining the Effect of Antisense PTI-1 Expression on the Biological Properties of PTI-1 Expressing Transformed and Tumorigenic Cells.

Antisense technology represents a potentially useful strategy for selectively inactivating specific target genes. To determine if suppression of PTI-1 expression could modify the transformed phenotype in LNCaP DNA-transfected nude mouse tumor-derived CREF-Trans 6 cells, CREF-Trans 6:4 NMT, antisense PTI-1 constructs were prepared in a Zeocin expression vector system. Transfection of CREF-Trans 6:4 NMT cells with a Zeocin-PTI-1 (AS) construct, but not with a Zeocin vector lacking the antisense PTI gene, and selection in Zeocin resulted in $Zeo^R$ colonies with a flat morphology (FIG. 1). Morphologically reverted PTI-1 (AS) containing CREF-Trans 6:4 NMT cells also displayed a suppression in anchorage independent growth (FIG. 2). Studies have been conducted to determine the in vivo tumorigenic properties in nude mice of PTI-1 (AS) containing CREF-Trans 6:4 NMT cells. When four anti-sense transfected flat revertant of CREF trans 6:4 NMT cells are injected into a thymic nude mice, tumor formation is prevented (FIGS. 3A & 3B). Additionally, the Zeocin PTI-1 (AS) construct has been transfected into DU-145 cells to determine its effect on in vitro transformation and in vivo oncogenicity in nude mice.

The above studies suggest that PTI-1 (AS) can effectively revert the transformed phenotype of cells expressing PTI-1. These observations suggest that further studies using adenovirus vectors, for gene delivery, are warranted. The use of adenovirus vectors to express therapeutic gene products has great potential, especially if the expression of the desired gene is only required transiently to suppress malignant cell growth, so that the natural defense mechanisms of the patient can gain the upper hand. Accordingly adenovirus vectors are being constructed to express RNAs corresponding to antisense sequences of PTI-1. The antisense version should suppress the oncogenic phenotype of CREF-Trans 6:4 NMT and human prostate carcinoma cells. The technique employed to create the adenovirus vectors is essentially that of Graham and his colleagues, in which a small bacterial plasmid, containing the left hand end of the adenovirus genome, is modified to encode the gene of choice under the control of a suitable mammalian promoter; with appropriate RNA processing signals also included. The cassette is then incorporated into the full length adenovirus genome using homologous recombination between the cassette plasmid and a cloned adenovirus genome, after co-transfection into human cells. Following co-transfection, the recombinant virus is plaque-purified and examined for expression of the desired gene product. Homologous recombination is the rate-limiting step in this method, and so we have modified the cassette plasmid to increase the available homology between it ant the full length genome. This has led to a considerably increased success rate in the construction of a range of vectors. The antisense versions of the whole PTI-1 gene and the 5' UTR region of this gene are being created. These vectors available will therefore be available for analysis soon.

C. Analyze PTI-1 Expression Using in Situ Hybridization Approaches in Prostate Carcinomas of Differing Degrees of Differentiation and Hormone Responsiveness Versus Prostatic Intraepithelial Neoplasia (PIN), Benign Prostatic Hypertrophy (BPH) and Normal Prostate Tissues.

A variety of optimally handled tissues suitable for expression analysis has now been obtained. These include samples of normal and hyperplastic prostate, in addition to prostate carcinomas exhibiting a range of differentiation varying from in situ, non-invasive carcinoma (PIN), too invasive well differentiated and invasive poorly differentiated tumors. The PTI-1 cDNA has been cloned into vectors suitable for riboprobe synthesis and in situ hybridization analysis. Probes prepared include portions of the PTI-1 5' UTR, in addition to the "bridge region" spanning the 5' UTR junction with the EF-1α homologous sequence. Sense PTI-1 and antisense PSA riboprobes are being used as experimental controls. Using these approaches initial experiments are under way to define the stages of transformation in prostate carcinoma with which PTI-1 expression is associated.

D. Otimizing the Use of PTI-1 as a Probe for Detecting Prostate Carcinoma Cells in the Peripheral Circulation of Patients.

Confirmation of the authenticity of PTI-1 by demonstrating the presence of the bridge region (5' UTR linked to EF-1α) was a priority for further translational studies on this interesting gene. Experiments have been performed to directly determine the relationship between PSA, PSM and PTI-1 expression using RT-PCR with RNAs isolated from peripheral blood from patients with and without confirmed metastatic carcinoma of the prostate. These studies documented that PTI-1 is more efficient in detecting patients with presumably metastatic prostatic carcinoma cell in the blood stream than either PSA or PSM (Sun, Y., Lin, J., Katz, A. E. & Fisher, P. B. (1997) Cancer Res. 57, 18–23.).

Third Series of Experiments

Differential Effect of PTI-1 Antisense Expression on Colony Formation in Normal Cloned Rat Embryo Fibroblast (CREF-Trans 6), Human Prostate Carcinoma DNA-Transformed CREF-Trans 6 and Ha-ras Oncogene-Transformed CREF Cells.

To determine if the effect of PTI-1 antisense [PTI-1 (AS)] is specific for cells expressing the PTI-1 gene or the 5' untranslated region of the PTI-1 gene (5' UTR) lipofectin-mediated transfection studies have been performed. The cell types used included CREF-Trans 6 (negative for PTI-1 expression), CREF-Trans 6:4 NMT (tumor-derived CREF-Trans 6 cells transfected with high molecular weight DNA from LNCaP human prostate cancer cells) (positive for PTI-1 expression) and CREF-ras (CREF cells transformed by the Ha-ras oncogene) (positive for expression of the unique 5' UTR of PTI-1).

Experimental Procedure: CREF-Trans 6, CREF-Trans 6:4 NMT and CREF-ras cells were seeded at $1 \times 10^6$ per 60 mm-plate and 24 hr later cultures were transfected using 50 mg per plate of lipofectin with 10 ug of pZeoSV vector DNA (conferring resistance to Zeocin) or pZeoSV-PTI-1 (AS) construct DNA (containing the PTI-1 gene in an antisense orientation in the pZeoSV vector). Forty-eight hr later, transfected cells were reseeded at $1 \times 10^5$ cells/60-mm plate and the next day the medium was changed with the addition of Zeocin (50 to 100 ug/ml). Cultures were refed with Zeocin-containing medium every 3 to 4 days and colonies were fixed and stained with Giemsa after 3 weeks culture. The average number of Zeocin-resistant colonies forming in 4 plates was determined and the ratio between vector and PTI-1 (AS) colony formation was determined.

Results:

| Cell Type | pZeoSV (Vector) | pZeoSV-PTI-1 (AS) | Ratio V/AS |
| --- | --- | --- | --- |
| CREF-Trans 6 | 71 ± 7 | 66 ± 7 | 1.1 |
| CREF-Trans6:4 NMT | 68 ± 7 | 30 ± 4 | 2.3* |
| CREF-ras | 37 ± 7 | 17 ± 3 | 2.2* |

*Significant reduction in colony formation in PTI-1 (AS) transfected versus pZeoSV transfected cultures.

Conclusion: Antisense PTI-1 can suppress colony formation in transformed and tumorigenic CREF-Trans 6 cells, whereas this effect is not observed in normal CREF-Trans 6 cells. Since CREF-Trans 6:4 NMT expresses the complete PTI-1 gene and CREF-ras only expresses the unique 5' UTR of PTI-1, inhibition of either a partial region of PTI-1 (5' UTR) or the complete PTI-1 gene using antisense technology can inhibit the growth and colony formation of tumorigenic transformed cells.

Fourth Series of Experiments

Transcription of the 5' Untranslated Region (5' UTR) of PTI-1 in Transformed Rodent and Human Cancer Cells Background: PTI-1 expression is detected using Northern blotting in human prostate carcinoma cell lines, human prostate carcinomas from patients and specific human carcinoma cell lines derived from the breast (T47D), colon (SW480 and LS174T) and lung (NCI H-69). In contrast, PTI-1 is not expressed in normal prostate tissue, benign prostate hypertrophy tissue, specific human cancer cell lines (such as the human melanoma cell line HO-1 and the specific strains of human breast carcinoma cell line MCF-7), various normal cell lines and CREF-Trans 6 cells. The ability to be expressed as mRNA suggests that the PTI-1 gene is being transcribed by the appropriate cell type. Studies have been conducted to determine if the 5' UTR of PTI-1 is expressed in additional cell types and if transformation by diverse oncogenes activates transcription of the 5' UTR of PTI-1.

Experimental Protocol: The transcription of the unique 5' UTR of PTI-1 was determined using nuclear run-on assays as previously described (1). Nuclei from approximately $2 \times 10^6$ cells were isolated and RNA previously initiated by RNA polymerase II were allowed to elongate in the presence of [$^{32}$P] UTP. Nuclear RNA was isolated, purified by filtering through a G-50 Sephadex column. Nuclear RNA was extracted, purified by filtering onto Millipore (0.45-um) filters followed by elution and denaturing by treatment with 0.1 M sodium hydroxide for 5 min on ice. Nylon membranes containing 2 μg of the appropriate denatured plasmid DNA gene insert were hybridized with [$^{32}$P]-labeled RNA from the different cell types as described (2,3).

Cell Types include:

CREF (cloned rat embryo fibroblast),

CREF-Ha-ras (CREF cells transformed by the Ha-ras oncogene),

CREF-HPV-51 (CREF cells transformed by the human papilloma virus-51 E6/E7 transforming genes)

CREF-V-src (CREF cells transformed by the V-src oncogene)

DU-145 (hormone refractive human prostate carcinoma cell line)

LNCaP (hormone responsive human prostate carcinoma cell line)

PC-3 (hormone refractive human prostate carcinoma cell line)

H0-1 (human melanoma cell line)

T47D (human breast carcinoma cell line)

DNA Probes include:

GAPDH-(glyceraldehyde phosphate dehydrogenase)

5' UTR-PTI-1 (5' UTR region of the PTI-1 gene)

pBR322 (bacterial negative control gene sequences)

Results: CREF cells contain transcripts for GAPDH, but not the 5' UTR of PTI-1 or pBR322. CREF cells transformed by the Ha-ras oncogene (CREF-Ha-ras), HPV-51 (CREF-HPV-51) and V-src (CREF-V-src) transcribe the GAPDH and the PTI-1 5' UTR sequences. All three prostate carcinoma cell lines, DU-145, LNCaP and PC-3, express GAPDH and the 5' UTR of PTI-1. The H0-1 human melanoma and the MCF-7 human breast carcinoma cell lines do not transcribe the 5' UTR of PTI-1. The human T47D breast carcinoma cell line contains transcripts for the 5' UTR of PTI-1.

Conclusion: Transformation of CREF cells by diverse oncogenes, that result in morphological transformation and acquisition of oncogenic potential, result in the activation of the 5' UTR of PTI-1. These results implicate expression of genes linked to this sequence as components of the transformation process. This sequence may therefore serve as a direct target for inactivation and reversal of the cancer phenotype. The 5' UTR of PTI-1 is transcriptionally active in prostate carcinoma and breast carcinoma cells containing mRNA for the PTI-1 gene. In contrast, no transcription or expression on a Northern level is apparent in H0-1 and T47D human cancer cells. These results demonstrate that expression of PTI-1 (both the 5' UTR region and the complete PTI-1 mRNA) is restricted to specific cancer cells, including 100% of prostate carcinoma cell lines and specific breast carcinoma cell lines). In this context, targeting the inactivation of the 5' UTR of PTI-1 and the full-length PTI-1 gene may prove useful for reversing the cancer phenotype. The absence of expression of this gene in normal cells suggests that antisense, and similar strategies, designed to inactivate the PTI-1 gene may prove useful for cancer therapy.

Refs.

1. Su, Z.-z., Yemul, S., Estabrook, A., Friedman, R. M., Zimmer, S. G., and Fisher, P. B. Transcriptional switching model for the regulation of tumorigenesis and metastasis by the Ha-ras oncogene: transcriptional changes in the Ha-ras tumor suppressor gene lysyl oxidase. Intl. J. Oncol., 7: 1279–1284, 1995.
2. Su, Z.-z., Austin, V. N., Zimmer, S. G., and Fisher, P. B. Defining the critical gene expression changes associated with expression and suppression of the tumorigenic and metastatic phenotype in Ha-ras-transformed cloned rat embryo fibroblast cells. Oncogene, 8: 1211–1219, 1993.
3. Jiang, H., Waxman, S., and Fisher, P. B. Regulation of c-fos, c-jun and jun-B gene expression in human melanoma cells induced to terminally differentiate. Mol. Cell. Different., 1: 197–214. 1993.

Fifth Series of Experiments

The genetic alterations and molecular events mediating human prostate cancer development and progression remain to be defined. Rapid expression cloning and differential RNA display detect a novel putative oncogene, prostate tumor inducing gene-1 (PTI-1), that is differentially expressed in human prostate (as well as breast, colon and small cell lung) cancer cell lines, patient-derived prostate carcinomas and blood from patients with metastatic prostate cancer. PTI-1 consists of a unique 5' untranslated region (5' UTR) with significant sequence homology to Mycoplasma hyopneumoniae 23S ribosomal RNA juxtaposed to a sequence that encodes a truncated and mutated human elongation factor 1α (Trun-EF). Stable expression of a near full-length 1.9 kb PTI-1 gene, but not the separate PTI-1 5' UTR or Trun-EF region, in normal rat embryo fibroblast cells, CREF-Trans 6, induces an aggressive tumorigenic phenotype in athymic nude mice. Blocking PTI-1 expression with antisense PTI-1 results in reversion of transformed PTI-1 expressing cells to a more normal cellular morphology with suppression in both anchorage independent growth and tumorigenic potential in athymic nude mice. These findings document that PTI-1 is indeed an oncogene and directly blocking PTI-1 expression can nullify cancer phenotypes. In these contexts, PTI-1 not only represents a gene with discriminating diagnostic properties but it may also serve as a novel target for the gene-based therapy of human prostate and other cancers.

Prostate cancer is the most frequently diagnosed internal cancer of men in the United States and the second leading reason for cancer-related male deaths (1–3). These statistics underscore the need for improved molecular staging of and therapeutic approaches for this prevalent neoplastic disease. Current procedures for detecting prostate cancer rely on physical examinations, monitoring serum prostate-specific antigen (PSA) levels, ultrasound, bone scans and tissue biopsy (1–3). Recent studies indicate that RT-PCR approaches using PSA specific primers and RNA isolated from blood may provide an early indicator of prostate cancer progression (4,5). However, all of these strategies are limited in both their sensitivity and specificity. In addition, they do not provide the discriminatory power necessary to distinguish between cancers that will remain localized and pose no imminent health threat and aggressive cancers resulting in progressive disease culminating in metastasis and death.

A rapid expression cloning strategy coupled with differential RNA display, screening of a human LNCaP cDNA expression library and the rapid amplification of cDNA ends (RACE) approaches identified a novel putative prostate carcinoma tumor inducing oncogene, PTI-1 (6–8). Expression of PTI-1 occurs in human prostate, breast, colon and lung carcinoma cell lines and patient-derived prostate carcinoma tissues, but not in normal prostate or benign hypertrophic prostate (BPH) tissues (7,8). The full-length PTI-1 cDNA is 2123 bp consisting of a unique 630-bp 5' UTR with significant homology to Mycoplasma hyopneumoniae 23S ribosomal RNA fused to a sequence that is a truncated and mutated human EF-1α (Trun-EF) (7). PCR with human genomic DNAs from normal human brain and kidneys, using PTI-1 specific 5' UTR primers, provides evidence that this novel sequence is present in the human genome (8). Support for this conclusion comes from Southern blotting of genomic DNAs. Moreover, RT-PCR, using one primer specific for the 5' UTR and the other for the EF-1α coding region, amplifies PTI-1 transcripts from total RNAs of prostate, breast and colon carcinoma cell lines and blood samples from patients with metastatic prostate cancer (8). Taken together these data suggest that the identification of PTI-1 was unlikely due to a contamination of samples with bacteria or cloning artifacts. Serial-dilution experiments indicate that PTI-1 can detect 1 prostate carcinoma cell in $10^8$ cells not expressing PTI-1 (8). The exquisite sensitivity of PTI-1 in detecting carcinoma cells in the bloodstream of patients with metastatic prostate cancer, suggests that this gene will prove extremely valuable as a sensitive and specific monitor of prostate cancer progression as reflected by the presence of cancer cells in a patient's bloodstream.

The objective of the present study was to resolve if PTI-1 expression simply correlates with or actually controls neoplastic transformation in the CREF-Trans 6 cell line. To define the role of PTI-1 in eliciting transformation of CREF-Trans 6 cells, both ectopic sense (S) expression and AS strategies were used. Expression constructs were produced that result in S or AS expression of specific components of the PTI-1 gene, i.e., the 5' UTR, Trun-EF and the 1.9 kb region of PTI-1 (including part of the 5' UTR and the Trun-EF). Pooled PTI-1 S expressing CREF-Trans 6 cells are tumorigenic in nude mice, whereas no tumors form when pooled 5' UTR or Trun-EF expressing CREF-Trans 6 cells are injected subcutaneously into nude mice. Transient transfection assays demonstrate that only the complete PTI-1 AS construct can inhibit colony formation in PTI-1 expressing cells, including LNCaP DNA transfected nude mouse tumor-derived CREF-Trans 6:4 NMT and human DU-145 cells. Stable PTI-1 AS expression in CREF-Trans 6:4 NMT cells results in a reversion in morphology to that of untransformed CREF-Trans 6 cells, an elimination of PTI-1 sense RNA, a reduction in anchorage-independence and a suppression in oncogenic potential in athymic nude mice. These results provide definitive evidence that PTI-1 is an oncogene and its expression is directly involved in controlling growth and maintaining the transformed phenotype. On the basis of the restricted expression of PTI-1 to carcinoma cells and the ability of AS molecules to directly inhibit expression of PTI-1 and the neoplastic phenotype, intervention in PTI-1 expression may represent a novel and effective approach for the therapy of human prostate and other PTI-1 expressing cancers.

Materials and Methods

Cell Lines, Culture Conditions and Anchorage-Independence Assays. The CREF-Trans 6 cell line and nude mouse tumor-derived CREF-Trans 6 cells transfected with LNCaP DNA, CREF-Trans 6:4 NMT, have been described previously (6). Human cell lines used in this study include: prostate carcinoma (DU-145 and LNCaP), breast carcinoma (MCF-7 and T47D) and colon carcinoma (SW480 and WiDr) (7,8). Rodent cells were grown in Dulbecco's modified Eagle's medium supplemented with 5% fetal bovine serum (DMEM-5) at 37° C. in a 95% air/5% $CO_2$-humidified incubator. Human cells were grown in DMEM supplemented with 10% fetal bovine serum (DMEM-10). Early passage (<5) normal human prostate epithelial (NHPE) cells were obtained from Clonetics Inc., CA and grown in serum-free medium supplied by the manufacturer. All cell lines used in the present study were tested for Mycoplasma contamination using the GenProbe Mycoplasma test kit (Gaithersburg, Md.) and found to be Mycoplasma free.

Expression vector constructs and DNA transfection assays. A 1.9 kb PTI-1 cDNA, containing an ~500-bp region from the 5' UTR, the Trun-EF coding region and the 3' UTR, was cloned in a sense (S) and antisense (AS) orientation into a pZeoSV vector as previously described (9,10). Additionally, a 500-bp region of the 5' UTR of PTI-1 and the Trun-EF of PTI-1 were also cloned in a S and AS orientation into a pZeoSV vector. To study the effects of these constructs on monolayer colony formation the vector (pZeoSV) containing no insert, PTI-1 S, PTI-1 AS, 5' UTR S, 5' UTR AS, Trun-EF S or Trun-EF AS expression constructs were transfected into the various cell types by the lipofectin method (GIBCO/BRL) and zeocin resistant colony formation or tumorigenic potential in nude mice was determined (10–12).

Anchorage-independence and tumorigenicity assays. Anchorage independence assays were performed by seeding various cell densities in 0.4% Noble agar on a 0.8% agar base layer both of which contain growth medium (13). Colonies of $\geq 0.1$ mm in diameter were identified with a calibrated grid under an Olympus inverted phase-contrast microscope after 21 days. Tumorigenesis assays were performed as described by injecting $1 \times 10^6$ cells subcutaneously into athymic BALB/c nude mice and monitoring animals for tumor development 2x per week (11–13).

RNA preparation and Northern blotting, nuclear run-on and RNase protection assays. Total cellular RNA was isolated by the guanidinium/phenol extraction method and Northern blotting was performed as described (9,10). Fifteen μg of RNA were denatured with glyoxal/DMSO and electrophoresed in 1% agarose gels, transferred to nylon membranes and hybridized sequentially with $^{32}$P-labeled PTI-1 5' UTR (500-bp region), Zeocin and GAPDH cDNA probes (9,10). Following hybridization, the filters were washed and exposed for autoradiography. The transcription rates of PTI-1 5' UTR, Trun-EF, pBR322 and GAPDH in CREF-Trans 6, CREF-Trans 6:4 NMT, 4NMT-Vector cl 1, 4NMT-PTI-1-AS cl 1, 4NMT-PTI-1-AS cl 8 and 4NMT-PTI-1-AS cl 10 was determined by nuclear run-on assays as described (12). RNase protection assays were performed using the Ambion Ribonuclease Protection Assay Kit (Ambion, Tex.). Briefly, antisense and sense RNA probes were made by in vitro transcription and labeled with 32P-UTP, hybridized with total cellular RNA and digested with a mixture of RNase A and RNase T1. After electrophoresis in 6% polyacrylamide gels and autoradiographic exposure the protected RNA fragments appeared as distinct bands of predicted molecular size (14,15).

Experimental Results and Discussions

PTI-1 Is a Dominant Acting Oncogene. To determine if PTI-1 has oncogenic properties, a 1.9 kb PTI-1 clone, missing ~215 bp from the 5' UTR of the original PTI-1 cDNA isolated from a human prostate LNCaP cDNA library, was cloned into a pZeoSV vector and transfected into CREF-Trans 6 cells. Transfectants were selected for zeocin resistance and pooled colonies from 4 separate plates were each injected into 4 athymic nude mice, total 16 nude mice. Within 10 days of injection, tumors were apparent in all animals (FIG. 5). As anticipated, nude mice injected with CREF-Trans 6:4 NMT cells, resulting from transfection with high molecular weight DNA from LNCaP cells and expressing PTI-1, also induced rapidly growing tumors (FIG. 5). Seven independent tumors derived from animals injected with pooled PTI-1 transfected CREF-Trans 6 cells were excised and established in cell culture. All of these tumor-derived cell lines exhibited a transformed morphology and expressed PTI-1 and the Zeocin gene (FIG. 6 and data not shown). No tumors developed when animals were injected with CREF-Trans 6 cells or CREF-Trans 6 cells transfected with an empty pZeoSV expression vector or pZeoSV expression vectors containing a 500 bp region of the 5' UTR of PTI-1, the Trun-EF of PTI-1 or a combination of the separated 500 bp 5' UTR and the Trun-EF regions of PTI-1 (FIG. 5). These results document that PTI-1 is a dominant acting oncogene and the intact gene is required to elicit a biological effect.

Expression of an Intact Antisense PTI-1 Gene Inhibits Monolayer Colony Formation in PTI-1 Expressing Cells. To scrutinize the role of PTI-1 in maintenance of transformation and the tumorigenic phenotype, an AS approach was used to selectively suppress expression of this gene. Transfection of PTI-1 AS (cloned in a pZeoSV vector permitting selection in Zeocin) into PTI-1 expressing cells, including CREF-Trans 6:4 NMT and DU-145, results in a>50% suppression in monolayer colony formation, average of three independent experiments (FIG. 7). Transfection of PTI-1 AS into T47D human breast carcinoma and SW480 human colon carcinoma cells that express PTI-1 also inhibits colony formation by >50% (data not shown). In contrast, only<10% inhibition in colony formation occurs following PTI-1 AS transfection of CREF-Trans 6 cells, that do not express PTI-1. Similarly, PTI-1 AS only inhibits colony formation by ~20% WiDr human colon carcinoma cells that do not contain PTI-1 mRNA (data not shown).

The PTI-1 cDNA consists of a unique 5' UTR with sequence homology to 23S rRNA from *Mycoplasma hyopneumoniae* adjacent to a Trun-EF (7,8). It was considered essential to determine if the effects on colony formation observed with the 1.9 kb AS PTI-1 gene were specific for this molecule or if a phenotypic response could also be induced with the AS 5' UTR or AS Trun-EF regions of PTI-1. This was of particular relevance, since the Trun-EF might alter the expression or functionality of endogenous EF-1α, thereby causing a nonspecific negative effect on protein synthesis and cell growth in cells not expressing PTI-1 (16–21). To approach this question, a 500 bp region of the 5' UTR and the Trun-EF of PTI-1 were subcloned in an AS orientation into the pZeoSV vector and transfected into CREF-Trans 6, CREF-Trans 6:4 NMT and DU-145 cells. In the case of CREF-Trans 6:4 NMT and DU-145, a maximum ~20% reduction in colony formation, three separate experiments, occurred following transfection with the AS 5' UTR or AS Trun-EF region of PTI-1 (FIG. 7). In CREF-Trans 6, transfection with AS 5' UTR or AS Trun-EF of PTI-1 inhibited colony formation by only<10% (three independent experiments) (FIG. 7). These findings illustrate that AS expression of an intact PTI-1 gene, but not an AS 5' UTR or AS Trun-EF, can specifically suppress growth in transformed cells expressing this gene. This suggests that inactivation of the specific fusion gene product, containing the 5' UTR and Trun-EF transcript, is mandatory for evoking the biological response described above.

It is noteworthy that only AS expression of an intact PTI-1 gene, but not an AS 5' UTR or Trun-EF construct, can revert the transformed phenotype and suppress colony formation in transformed rodent and human cancer cells expressing PTI-1. As previously discussed, the PTI-1 5' UTR shares significant homology with prokaryotic ribosomal RNA, and its coding region is 97% homologous to human EF-1α. A possible explanation for the lack of activity of the incomplete PTI-1 AS gene constructs may involve competitive interactions of the AS 5' UTR or AS Trun-EF PTI-1 molecules with endogenous ribosomal and EF-1α RNA messages, respectively. This competitive interaction with endogenous transcripts would predictably reduce the concentration of AS molecules to subthreshold levels that are unable to modify PTI-1 activity and alter cellular phenotypes. Alternatively, the differential effect of the intact PTI-1 AS versus the 5' UTR AS and Trun-EF AS regions of PTI-1 may reflect the complex interactions between AS and their cellular target molecules that are necessary for inhibiting gene expression and eliciting a biological response. This may include conformational requirements for the AS molecules that are mandatory for appropriate interaction with their cognate S counterparts. There are precedents indicating that not all AS oligonucleotides, even with comparable structures, exhibit predicted effects on expression of their target gene (14). Experiments are in progress to define small regions of the PTI-1 gene, such as the bridge region consisting of 5' UTR and Trun-EF nucleotides, that may provide useful targets for AS applications. Further research addressing these issues will be crucial for designing appropriate AS PTI-1 molecules for cancer therapeutics.

Antisense Inhibition of PTI-1 Expression Suppresses Transformation In vitro. PTI-1 expressing CREF-Trans 6:4 NMT cells display a transformed morphology that easily distinguishes them from untransformed CREF-Trans 6 cells (FIG. 1). Transfection of these cells with an intact AS PTI-1 results in the formation of colonies morphologically resembling untransformed CREF-Trans 6 (FIG. 1). This morphology change is not apparent in CREF-Trans 6:4 NMT cells transfected with the pZeoSV vector (FIG. 1). Similarly, the morphology of CREF-Trans 6:4 NMT cells is unaltered following transfection with an AS 500 bp PTI-1 5' UTR, an AS PTI-1 Trun-EF or a combination of the separate AS 500 bp PTI-1 5' UTR and an AS PTI-1 Trun-EF (data not shown).

Studies were performed to determine if the morphological reversion of AS PTI-1 expressing CREF-Trans 6:4 NMT cells correlates with specific changes in cellular phenotype. Eleven morphologically-reverted Zeocin resistant colonies of CREF-Trans 6:4 NMT cells transfected with AS PTI-1 were isolated and maintained as independent clonal cell lines. The majority of clones, 7 of 11, retained their CREF-Trans 6-like morphology even after repeated subculture (>20 passages). When tested for anchorage independent growth, CREF-Trans 6:4 NMT and six independent CREF-Trans 6:4 NMT pZeoSV vector transformed clones grew in agar with an ~40% efficiency (FIG. 2 and data not shown). In contrast, the majority of AS PTI-1 transfected CREF-Trans 6 clones exhibited a reduction in agar growth to<10% (FIG. 2). Repeated passage in monolayer culture of two originally CREF-Trans 6-like PTI-1 transfected CREF-Trans 6:4 NMT clones, 4NMT-PTI-1-AS cl 2 and cl 5, resulted in reappearance of cells with transformed morphology and these cells grew in agar with an intermediate or a similar efficiency as CREF-Trans 6:4 NMT and CREF-Trans 6:4 NMT pZeoSV vector transformed clones (FIG. 2). RNase protection assays document that 4NMT-PTI-1-AS cl 2 and cl 5 cells do not contain PTI-1 AS mRNA (data not shown). These results confirm that stable expression of AS PTI-1 can induce a reversion in the transformed properties of CREF-Trans 6:4 NMT cells as established by altered morphology and suppression of anchorage-independence.

Stable Expression of Antisense PTI-1 Inhibits Oncogenesis. On the basis of the in vitro suppression of transformation by AS PTI-1, studies were performed to determine if stable AS PTI-1 expression in CREF-Trans 6:4 NMT modifies oncogenic potential. CREF-Trans 6:4 NMT cells form rapidly growing tumors when injected subcutaneously into athymic nude mice (FIG. 3A). Transfection with the pZeoSV vector does not alter the tumorigenic potential of CREF-Trans 6:4 NMT cells. In contrast, AS PTI-1 transformed CREF-Trans 6:4 NMT cl 1, cl 6, cl 8 and cl 10, display a dramatic inhibition in tumor formation. In all cases, the majority of animals inoculated with the AS construct remained tumor-free during the course of the study, a minimum of 60 days. These results illustrate that AS PTI-1 also suppresses the oncogenic phenotype in vivo. In this context, gene targeting strategies using AS PTI-1 may prove amenable for the therapy of prostate and other cancers.

Mechanism by Which Antisense PTI-1 Reverses Cancer Phenotypes. The ability of AS PTI-1 to alter the phenotype of CREF-Trans 6:4 NMT cells could result from a specific effect of the AS on PTI-1 expression or it could involve a trivial non-specific effect occurring independent of alterations in PTI-1 RNA. To confirm that AS PTI-1 is expressed and it is altering PTI-1 RNA levels in morphologically reverted CREF-Trans 6:4 NMT cells, RNase protection assays were conducted (FIG. 8). A PTI-1 sense transcript of 357 nt and a PTI-1 AS transcript of 465 nt was synthesized and the ability of these probes to protect in vivo produced RNA species was determined (14,15). In the case of the 357 nt PTI-1 sense transcript, protection is only observed in the AS PTI-1 expressing CREF-Trans 6:4 NMT clones, i.e., 4NMT-PTI-1-AS cl 1, cl 8 and cl 10 (FIG. 8). As anticipated the 357 nt protected fragment was not apparent in CREF-Trans 6:4 NMT, 4NMT-Vector cl 1, LNCaP, DU-145 or CREF-Trans 6 cells lacking the AS PTI-1 transcripts. When the RNase protection assay was performed using a 465 nt AS transcript, protection is observed in LNCaP, DU-145 and CREF-Trans 6:4 NMT cells that contain PTI-1 sense transcripts. Absence of PTI-1 RNA results in no protection of the 465 nt AS probe. As predicted, the 465 nt AS protected band is not present in the three PTI-1 AS expressing CREF-Trans 6:4 NMT clones or in control CREF-Trans 6 cells. These results establish that expression of AS PTI-1 in morphologically reverted CREF-Trans 6:4 NMT cells correlates with absence of the PTI-1 message.

AS inhibition of gene expression can work at multiple levels, including altering transcription of a target gene, facilitating the degradation of targeted double-stranded mRNA and/or inhibiting binding of the mRNA to the ribosome preventing translation into protein (22–24). As demonstrated using RNase protection assays, AS PTI-1 prevents the appearance of PTI-1 mRNA in reverted clones. To determine if the stable expression of AS PTI-1 can also modify transcription of the PTI-1 gene nuclear run-on assays were performed (FIG. 9). The relative rate of RNA transcription from the 5' UTR of PTI-1 is inhibited ~2 to 3-fold in AS PTI-1 expressing CREF-Trans 6:4 NMT cl 1, cl 8 and cl 10 in comparison with vector-transformed and parental CREF-Trans 6:4 NMT cells. No transcription of the 5' UTR is detected in CREF-Trans 6 cells. A similar ~2 to 3-fold reduction in transcription is also apparent in the AS PTI-1 expressing clones when hybridized with the Trun-EF gene sequence (FIG. 9). Because of high sequence homology between the Trun-EF of PTI-1 and endogenous rat EF-1$\alpha$ (~91 to 94% homologous with different rat species) cross-hybridization can be anticipated. Therefore, the apparent decrease in transcription of the Trun-EF region of PTI-1 does not definitively prove that transcription of this gene is suppressed in these cells. These results confirm that only small changes in the transcription of PTI-1 occur in the AS PTI-1 expressing cells, suggesting that the predominant effect of AS PTI-1 is on steady-state mRNA levels. These changes could include alterations in tanscriptional initiation, transcriptional attenuation and/or message stability.

Proposed Hypothetical Model of Action of PTI-1 as an Oncogene. Cancer is a progressive disease characterized by the appearance of new traits or the further elaboration of existing transformation related properties in the evolving tumor cells (25–27). Recent data provide compelling evidence for a potential link between alterations in the translational machinery of cells, including both eukaryotic initiation and elongation factors, and oncogenesis (28,29). Overexpression of the eukaryotic protein synthesis initiation factor, eIF-4E, can profoundly affect cellular physiology, including cooperating with viral oncogenes (such as v-myc and adenovirus E1A) to transform primary rodent cells (30), eliciting a tumorigenic phenotype in established rodent cells (31) and cooperating with MAX to produce a tumorigenic and metastatic phenotype in Chinese hamster ovary (CHO) cells (32). Elevated expression of EF-1$\alpha$, that normally functions to insure proper codon-anticodon binding interactions at the A site of the ribosome (28,29), also modifies cellular properties rendering both mouse and Syrian hamster cells susceptible to carcinogen- and ultraviolet light-induced transformation (33). Enhanced levels of EF-1$\alpha$ are also found in tumors of the pancreas, colon, breast, lung, and stomach relative to adjacent normal tissue (34). Moreover, the data in the present paper provides direct experimental support for an association between the expression of a truncated and mutated EF-1$\alpha$, encoded by PTI-1, and expression of cancer phenotypes.

On the basis of studies in bacteria (elongation factor-Tu) and yeast (EF-1$\alpha$), a model of action of EF-Tu/EF-1$\alpha$ has been proposed (16–21,35). These molecules are perceived to mediate the process of kinetic protein proofreading that controls appropriate codon-anticodon binding interactions (16). Specific mutations in EF-Tu elicit dominant-negative inhibition of protein synthesis and increase missense error rates in bacteria (16–19). Similarly, mutations (specific amino acid and altered expression) in EF-1$\alpha$ in yeast directly affect frequencies of frameshifting and amino acid misincorporations, proofreading of codon-anticodon interactions and suppression of nonsense mutations (20,21). These findings support a potential hypothesis for the action of PTI-1 that involves a process we have termed "translational infidelity" (7). In this model, PTI-1 modifies EF-1$\alpha$ activity to introduce distinct amino acid mistakes generating mutant transforming proteins and/or preventing cancer cells from correcting specific protein mutations that promote cancer progression (7). Studies are now being conducted using Saccharomyces cerevisiae and genetically engineered mammalian cells as experimental model systems to resolve the role of PTI-1 in regulating protein translation and cellular phenotype.

The mechanism by which PTI-1 functions as an oncogene requires clarification. However, this observation provides additional support for an association between protein translational control and the neoplastic process (7,28–34). As discussed above, on the basis of structure, PTI-1 may mediate carcinoma formation from epithelial precursor cells by modifying normal EF-1$\alpha$ function in a dominant-negative is manner, thereby, resulting in decreased protein translational fidelity and an inability to repress specific mutations in cancer cells (28,29). If the "translational infidelity" hypothesis is proven accurate, PTI-1 may represent a novel class of genes that can directly effect "genomic stability" and function as an important contributor to the mutator phenotype of cancer cells and tumor progression by altering the accuracy of protein translation. At present this possibility is only hypothetical. The PTI-1 oncogene may have developed as a consequence of specific mutations in EF-1$\alpha$ including a fusion with 5' UTR sequences with homology to bacterial 23S ribosomal RNA (7,8). Since the unique 5' UTR of PTI-1 is found in the genomes of both normal and cancer cells, it will be important to isolate and compare the genomic structure of these genes. An evaluation and analysis of these genetic elements should provide important insights into the potential origin and role of PTI-1 in cancer.

Conclusion. The PTI-1 gene represents a significant advance in monitoring prostate carcinoma progression as indicated by the occurrence of prostate carcinoma cells in a patients' circulatory system (8). We presently provide compelling evidence that the PTI-1 gene is a dominant-acting oncogene and it can serve as a direct target for intervening in the cancer phenotype. On the basis of structure, i.e., encoding a truncated and mutated human EF-1$\alpha$, the PTI-1 gene represents the first member of a new class of oncogenes. These data provide support for the hypothesis that PTI-1 is a functionally relevant genetic component of prostate (and possibly breast, colon and lung) cancer development and progression and targeting this gene for inactivation may represent a novel strategy for intervening in the cancer process.

References of the Fifth Series of Experiments
1. Epstein, J. I., Pizov, G. & Walsh, P. C. (1993) *Cancer* 71, 3582–3593.
2. Mukamel, E., Hanna, J. & deKernion, J. B. (1987) *Urology* 30, 318–323.
3. Salo, J. O., Kivisaari, L., Rannikko, S. & Lehtonen, T. J. (1987) *J. Urol.* 137, 435–438.
4. Katz, A. E., Olsson, C. A., Raffo, A. J., Cama, C., Pelman, H., Seaman, E., O'Toole, K. M., McMahon, D., Benson, M. C. & Butyan, R. (1994) *Urology* 43, 765–775.
5. Israeli, R. S., Miller, W. H. Jr., Su, S. L., Powell, T., Fair, W. R., Samadi, S. D., Huryk, R. F., DeBlasio, A., Edwards, E. T., Wise, G. J. & Heston, W. D. W. (1994) *Cancer Res.* 54, 6306–6310.
6. Su, Z.-z., Olsson, C. A., Zimmer, S. G. & Fisher, P. B. (1992) *Anticancer Res.* 12, 297–304.
7. Shen, R., Su, Z.-z., Olsson, C. A. & Fisher, P. B. (1995) *Proc. Natl. Acad. Sci. USA* 92, 6778–6782.

8. Sun, Y., Lin, J., Katz, A. E. & Fisher, P. B. (1997) *Cancer Res.* 57, 18–23.
9. Jiang, H., Lin, J., Su, Z.-z., Kerbel, R. S., Herlyn, M., Weissman, R. B., Welch, D. & Fisher, P. B. (1995) *Oncogene* 10, 1855–1864.
10. Jiang, H., Su, Z.-z., Lin, J. J., Goldstein, N. I., Young, C. S. H. & Fisher, P. B. (1996) *Proc. Natl. Acad. Sci. USA* 93, 9160–9165.
11. Babiss, L. E., Zimmer, S. G. & Fisher, P. B. (1985) *Science* 228, 1099–1101.
12. Su, Z.-z., Austin, V. N., Zimmer, S. G. & Fisher, P. B. (1993) *Oncogene* 8, 1211–1219.
13. Fisher, P. B., Bozzone, J. & Weinstein, I. B. (1979) *Cell* 18, 695–705.
14. Duigou, G. J., Babiss, L. E., Iman, D. S., Shay, J. W. & Fisher, P. B. (1990) *Mol. Cell. Biol.* 10, 2027–2034.
15. Duigou, G. J., Su, Z.-z., Babiss, L. E., Driscoll, B., Fung, Y. K. & Fisher, P. B. (1991) Oncogene 6, 1813–1824.
16. Merrick, W. C. (1992) *Microbiol. Rev.* 60, 291–315.
17. Hwang, Y. W., Sanchez, A. & Miller, D. L. (1989) *J. Biol. Chem.* 264, 8304–8309.
18. Tapio, S. & Kurland, C. G. (1986) *Mol. Gen. Genet.* 205, 186–188.
19. Hughes, D., Atkins, J. F. & Thompson, S. (1987) *EMBO J.* 6, 4235–4239.
20. Sandbaken, M. G. & Culbertson, M. R. (1988) *Genetics* 120, 923–934.
21. Song, J. M., Picologlou, S., Grant, C. M., Firoozan, M., Truite, M. F. & Liebman, S. (1989) *Mol. Cell. Biol.* 9, 4571–4575.
22. Neckers, L., Whitesell, L., Rosolen, A. & Geselowitz, D. A. (1992) *Crit. Rev. Oncog.* 3, 175–231.
23. Toulme, J.-J. & Helene, C. (1988) *Gene* 72, 51–58.
24. Stein, C. A. & Cheng, Y.-C. (1993) *Science* 261, 1004–1012.
25. Fisher, P. B. (1984) in *Tumor Promotion and Cocarcinogenesis In Vitro: Mechanisms of Tumor Promotion*, ed. Slaga, T. J. (CRC, Boca Ration, Fla.), pp. 57–123.
26. Loeb, L. A. (1994) *Cancer Res.* 54, 420–424.
27. Rabbitts, T. H. (1994) *Nature* (London) 372, 143–149.
28. Riis, B., Rattan, S. I. S., Clark, B. F. C. & Merrick, W. C. (1990) *Trends Biochem. Sci.* 15, 420–424.
29. Sonnenberg, N. (1993) *Curr. Biol.* 5, 955–960.
30. Lazaris-Karatzas, A. & Sonenberg, N. (1992) *Mol. Cell. Biol.* 12, 1234–1238.
31. Lazaris-Karatzas, A., Montine, K. S. & Sonenberg, N. (1990) *Nature* (London) 345, 544–547.
32. De Benedetti, A., Joshi, B., Graff, J. R. & Zimmer, S. G. (1994) *Mol. Cell. Different.* 2, 309–334.
33. Tatsuka, M., Mitsui, H., Wada, M., Nagata. A., Nojima. H. & Okayama, H. (1992) Nature (London) 359, 333–336.
34. Grant, A. G., Flomen, R. M., Tizard, M. L. V. & Grant, D. A. W. (1992) *Int. J. Cancer* 51, 740–745.
35. Bourne, H. R., Sanders, D. A. & McCormick, F. (1991) *Nature* (London) 349, 117–127.

Sixth Series of Experiments

Previous studies demonstrate that an antisense gene construct targeting the majority (1.9 kb) of the PTI-1 molecule results in a suppression of oncogenic phenotype. In contrast, antisense directed toward only the 5' UTR or the trucated EF-1α region of PTI-1 does not elicit this phenotype. Three results argue that antisense inhibition of cancer phenotypes requires antisense molecules directed toward both the 5' UTR and the EF-1α region of PTI-1. To test this hypothesis antisense phosphorothioate oligonucleotides were constructed based on the sequence of the bridge specific probe (Sun, Y., Lin, J., Katz, A. E. & Fisher, P. B. (1997) *Cancer Res.* 57, 18–23.) region of PTI-1 (5'AAATTAAGCTATGCAGTCGG3'), BSP-AS. When CREF-trans 6 cells transformed by LNCaP human prostate cancer DNA and expressing the PTI-1 gene or DU-145 hormone refractive human prostate cancer cells are seeded in agar in the presence of as little as 2 µM of BSP-As both the size and number of colonies forming are decreased. The effect of the BSP-AS is dose-dependent resulting in very few colonies formed when cells are grown in ≧50 µM of this antisense oligonucleotide. These results provide direct evidence for the potential use of the BSP-AS for inhibiting transformation-related properties in tumor cells expressing PTI-1.

What is claimed is:

1. A composition comprising an antisense nucleic acid molecule which is complementary to (i) the 5' untranslated region of the Prostate Tumor Inducing-1 gene and (ii) the truncated EF-1α region of the Prostate Tumor Inducing-1 gene, wherein the nucleic acid molecule comprises a phosphorothioate linkage.

2. The composition of claim 1, where the antisense nucleic acid molecule is complementary to the frill-length Prostate Tumor Inducing-1 gene cDNA.

3. The composition of claim 1, where the antisense nucleic acid molecule is an oligonucleotide.

4. The composition of claim 3, wherein the oligonucleotide comprises an antisense oligonucleotide that is complementary to the bridge specific probe region of the Prostate Tumor Inducing-1 gene having a sequence 5' AAAT-TAAGCTATGCAGTCGG 3', as set forth in SEQ ID NO:1.

5. A composition comprising a first nucleic acid molecule encoding, in antisense orientation, a second nucleic acid molecule which is complementary to (i) the 5' untranslated region of the Prostate Tumor Inducing-1 gene and (ii) the truncated EF-1α region of the Prostate Tumor Inducing-1 gene.

6. The composition of claim where in the second nucleic acid molecule is complementary to the entire full-length Prostate Tumor Inducing-1 gene cDNA.

7. The composition of claim 6 wherein first nucleic acid molecule in contained in a vector.

8. The composition of claim 7 wherein the vector is a viral vector comprising a full length Prostate Tumor Inducing-1 cDNA, in antisense orientation, operatively linked to a promoter element.

* * * * *

SEQUENCE LISTING

```
<160> NUMBER OF SEQ ID NOS:  1

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:   Synthetic
      Oligonucleotide primer.

<400> SEQUENCE: 1
aaattaagct atgcagtcgg                                                    20
```